United States Patent [19]
Cheiky-Zelina et al.

[11] Patent Number: 6,028,433
[45] Date of Patent: *Feb. 22, 2000

[54] PORTABLE FLUID SCREENING DEVICE AND METHOD

[75] Inventors: Margaret A. Cheiky-Zelina, Cleveland; Wayne A. Bush, Wooster, both of Ohio

[73] Assignee: Reid Asset Management Company, Willoughby Hills, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 08/855,911

[22] Filed: May 14, 1997

[51] Int. Cl.$^7$ .................................................. G01R 27/26
[52] U.S. Cl. .......................... 324/663; 324/672; 324/688
[58] Field of Search .................................... 324/663, 639, 324/636, 672, 637, 688, 316

[56] References Cited

U.S. PATENT DOCUMENTS

| | | | |
|---|---|---|---|
| 4,646,070 | 2/1987 | Yasuhara | 340/603 |
| 4,689,553 | 8/1987 | Haddox | 324/58.5 |
| 5,025,222 | 6/1991 | Scott et al. | 324/639 |
| 5,103,181 | 4/1992 | Gaisford et al. | 324/637 |
| 5,260,665 | 11/1993 | Goldberg et al. | 324/636 |
| 5,262,732 | 11/1993 | Dickert et al. | 324/672 |
| 5,334,941 | 8/1994 | King | 324/637 |
| 5,548,217 | 8/1996 | Gibson et al. | 324/316 |
| 5,604,441 | 2/1997 | Freese et al. . | |
| 5,754,055 | 5/1998 | McAdoo | 324/636 |

OTHER PUBLICATIONS

International Search Report, dated Jan. 20, 1999 for PCT/US98/09039, International Filing Date May 8, 1998.
Iotech Catalog, p. 65, Jan. 1995.
"Model 958PF On–Line Ferrograph", *Foxboro Analytical*, (no month available) 1980 4 pgs.
958PF Series On–Line Ferrograph Installation and Operation, The Foxboro Company, (no month available) 1980, 6 pgs.
Particle Quantifier PQ (90) & PQ (90A), Predict Technologies, (no date).
Journal Reprints, The British Institute of Non–Destructive Testing, M.H. Jones and A. R. Massoudi, INSIGHT, vol. 37 No. 8, Aug., 1995, pp. 606–610.
Basics of Measuring the Dielectric Properties of Materials, Hewlett Packard, (no month available) 1992, No. 1217–1.
The Nist 60–Millimeter Diameter Cylindrical Cavity Resonator: Performance Evaluation for Permittifity Measurements, Eric J. Vanzura, Richard G. Geyer and Michael D. Janezic, Aug. 1993, National Institue of Standards and Technology Technical Note.
VISI Micons MIcron CONtaminant Sensor, VISI V–Tech Sensors, Inc., 3 pgs, (no date).

*Primary Examiner*—Josie Ballato
*Assistant Examiner*—Jose M. Solis
*Attorney, Agent, or Firm*—Renner, Otto, Boisselle & Sklar, P.L.L.

[57] ABSTRACT

This invention relates to a fluid screening device, comprising: an impedance sensor including a cavity for holding a fluid to be screened, an impedance of the impedance sensor being affected by conditions of the fluid; an impedance measuring circuit for measuring the impedance of the impedance sensor with respect to at least one frequency; a processor for processing impedance data taken by the impedance measuring circuit for purposes of determining a condition of the fluid; and a connector which operatively couples the impedance sensor to the impedance measuring circuit, the connector allowing the impedance sensor to be selectively detached from the impedance measuring circuit.

30 Claims, 13 Drawing Sheets

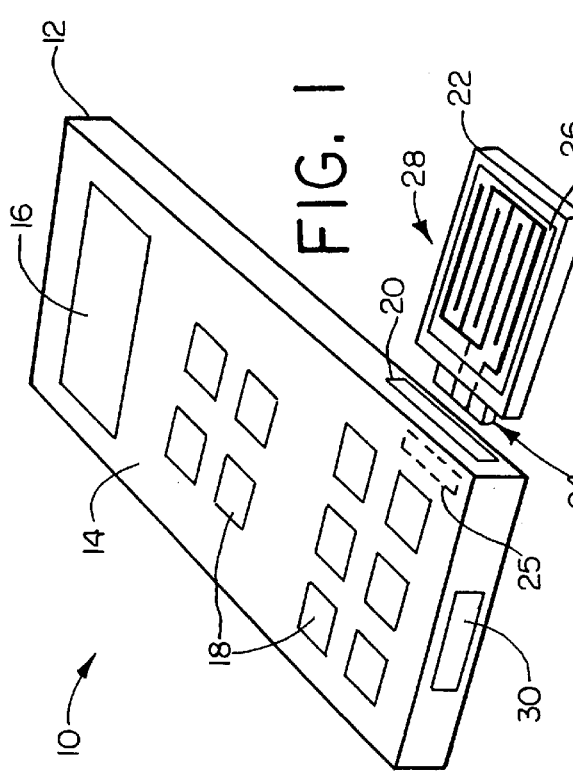
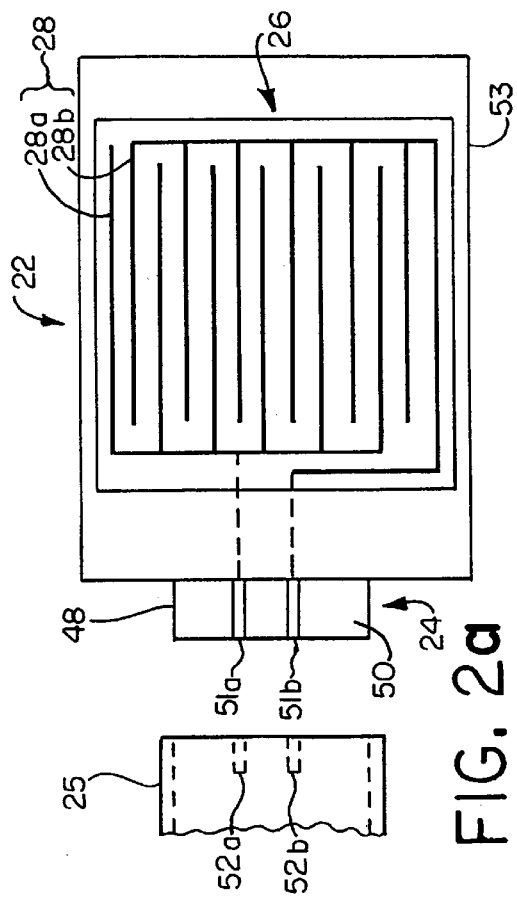
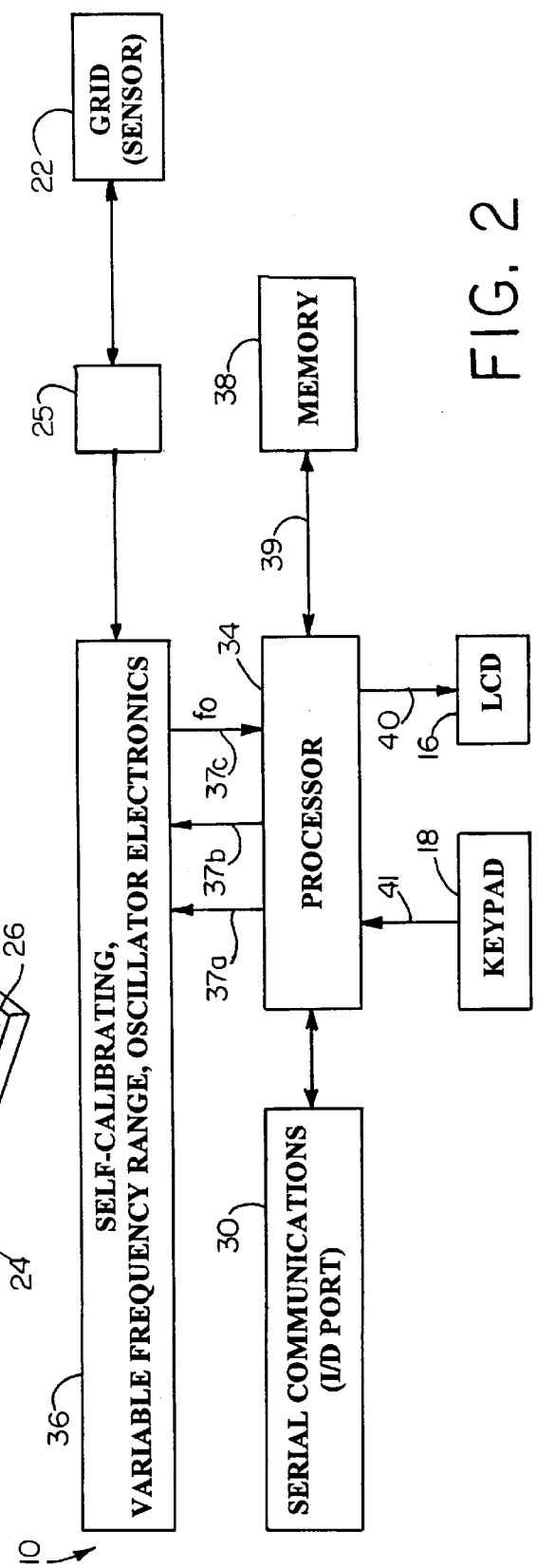

$$Z_c = \frac{R}{1+jwCR}$$

PORTABLE FLUID SCREENING DEVICE AND METHOD

FIELD OF THE INVENTION

The present invention relates generally to an apparatus and method for analyzing fluids such as lubricants. More particularly, the invention relates to a portable screening device for detecting and monitoring conditions of a fluid such as water content, soot, oxidation, corrosive products, and metallic or conductive particle contamination.

BACKGROUND OF THE INVENTION

The presence of corrosive products, contaminants, metallic particles, oxidation, etc., in fluids such as lubricants can cause problems. For example, contaminants in lubricants can lead to damage of machinery in which the lubricant is utilized, causing unnecessary or accelerated wear on the lubricated members.

Various approaches have been developed to detect conditions such as deterioration or contaminants in fluids. One conventional system described in U.S. Pat. No. 4,646,070 utilizes a pair of capacitor electrodes positioned in a fluid. The fluid serves as a dielectric between the electrodes to develop a frequency voltage signal across the capacitor electrodes. Based on such signal, the dielectric and deterioration of the fluid is determined. This solution suffers from a drawback in that it does not inform a user of the specific type or the magnitude of contamination in the fluid.

U.S. Patent No. 5,262,732 describes a system which utilizes an oscillator circuit coupled to a capacitive sensor. The fluid under test is placed in the capacitive sensor and the oscillator circuit generates a signal having a frequency that increases or decreases depending on the capacitance of the sensor. By analyzing the capacitance (via the oscillator output frequency) over a delay period, deteriorization of the fluid under test is evaluated. The output frequency is sampled over the time period, wherein the output frequency is measured a) with an electromagnet on in a first magnetization direction, b) with the electromagnet on in a second magnetization direction, and c) with the electromagnet off. Corrosion, contamination and ferromagnetic particulate data is deduced by analyzing the oscillator frequency with respect to time over the delay period.

The system described in the aforementioned U.S. Pat. No. 5,262,732 is rather large and cumbersome and does not lend itself to portability. In the field, it would be difficult to transport the device from machine to machine to analyze the lubricant at the location of the machinery, for example. In addition, it is advisable that the capacitive sensor which holds the fluid under test be cleaned carefully prior to each test. Unfortunately, this results in inconvenience as well as increased labor costs, etc.

In view of the aforementioned shortcomings associated with existing systems for analyzing conditions of a fluid such as a lubricant, there is a strong need in the art for a fluid screening device which provides detailed information regarding the particular types of contamination, degree of oxidation or other deterioration, etc. Moreover, there is a strong need in the art for such a screening device which is portable and which does not necessitate frequent cleaning of the sensor.

SUMMARY OF THE INVENTION

The fluid screening device and method of the present invention detects and monitors conditions of an oil or other fluid such as water content, soot, oxidation, corrosive products and ferromagnetic particulate contamination. The device analyzes the fluid under test in a plurality of different frequency bands to determine a condition of the fluid. The fluid under test is placed in an impedance sensor, e.g., a capacitive grid which serves as a component capacitor within an oscillator circuit. The fluid composition affects the capacitance (and therefore the impedance) of the capacitive grid, which in turn affects an output oscillation frequency of the oscillator circuit. The output oscillation frequency is evaluated over a plurality of frequencies and preferably in at least each of a high, medium and low frequency band. Based on the data collected over the frequency range, conditions of the fluid are determined with useful precision. The information is then stored in the device itself and/or in an external device and can be utilized for trending analysis.

Furthermore, in accordance with the present invention the capacitive grid or sensor in the fluid screening device is detachable from a main housing. The sensor may be disposable, thereby eliminating the need to clean the sensor prior to each evaluation. Preferably, the fluid screening device is contained within a hand-held housing for increased portability. Data obtained from fluid samples is stored in memory within the device and can be subsequently analyzed within the device or downloaded to a personal computer or other external device for detailed analysis with respect to trending, etc.

According to one aspect of the invention, a method of screening a fluid for contaminants includes using the fluid as a dielectric, measuring a property of the dielectric over a plurality of frequencies, and determining a fluid contamination status based on the dielectric property over the plurality of frequencies. The dielectric property may be an impedance magnitude and may be utilized to indicate the presence, if any, of contaminants in the fluid.

In an alternative embodiment, the fluid screening device and method of the invention evaluates the complex impedance presented by a fluid under test across a frequency band in order to determine more accurately the conditions of the fluid. The fluid under test is placed in an impedance sensor such as a capacitive grid and subjected to various different signal frequencies while measuring the corresponding impedance. Based on the measured impedance, the conditions of the fluid (e.g., oxidation, particulate concentration, etc.) can be determined with useful precision. The information is then stored and can be utilized for trending analyses, etc.

According to another aspect of the invention, a fluid screening device includes a capacitive grid or sensor having a cavity for holding a fluid to be screened, an impedance of the sensor being affected by conditions of the fluid; an impedance measuring circuit for measuring the impedance of the impedance sensor with respect to at least one frequency; a processor for processing impedance data taken by the impedance measuring circuit for purposes of determining a condition of the fluid; and a connector which operatively couples the impedance sensor to the impedance measuring circuit, the connector allowing the impedance senor to be selectively detached from the impedance measuring circuit.

According to still another aspect of the invention, a fluid screening device includes an impedance sensor including a cavity for holding a fluid to be screened, an impedance of the impedance sensor being affected by conditions of the fluid; an impedance measuring circuit for measuring the impedance of the impedance sensor; and a processor for processing impedance data obtained by the impedance measuring circuit for purposes of determining a condition of the fluid, wherein the impedance measuring circuit obtains the impedance over a plurality of frequencies as provided by the variable frequency generator.

To the accomplishment of the foregoing and related ends, the invention comprises the features hereinafter fully described and particularly pointed out in the claims. The following description and drawings set forth in detail certain illustrative embodiments of the invention. These embodiments are indicative however, of merely a few of the various ways in which the principles of the invention may be employed. Other objects and advantages of the invention will become apparent from the following detailed description of the invention when considered in conjunction with the drawing.

BRIEF DESCRIPTION OF THE DRAWINGS

FIG. 1 is a perspective diagram illustrating a portable, handheld fluid screening device in accordance with the present invention.

FIG. 2 is a block diagram of the fluid screening device in accordance with a first embodiment of the present invention, wherein the device analyzes fluids in a plurality of frequency bands to determine a condition of the fluid.

FIGS. 2a and 2b are top and side views, respectively, of a disposable capacitive sensor for use in the fluid screening device in accordance with the present invention.

DETAILED DESCRIPTION OF THE INVENTION

Figure 2B:
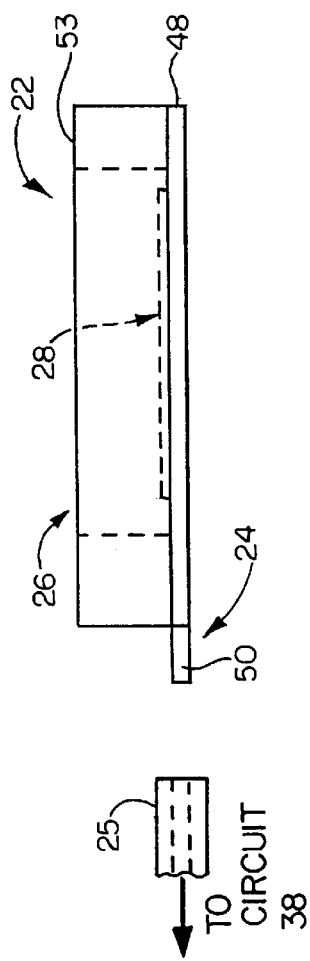

The present invention will now be described with reference to the drawings wherein like reference numerals are used to refer to like elements throughout. As will become more apparent based on the following description, the portable fluid screening device of the present invention utilizes the relationship between the impedance characteristics of the fluid under test and the condition of the fluid. In a first embodiment, the fluid screening device relies on a dependence of an oscillator output on a measured impedance (e.g., capacitance) by identifying the impedance magnitude in a plurality of frequency bands to identify contaminants and/or deterioration in fluids. In an alternative embodiment of the invention, the fluid screening device utilizes a frequency relationship of a complex impedance to identify contaminants and/or deterioration in fluids. In the case of a lubricating fluid, a small sample of the lubricant is taken and preferably is analyzed on location using the device. The sample is placed in a disposable impedance grid or sensor described more fully below which is connected to an oscillator circuit within the device. Alternatively, a complex impedance of the fluid sample is measured across a range of frequencies and stored. The real and imaginary components of the impedance as represented by the measured magnitude and phase of the impedance across the frequency range are subsequently compared with predetermined characteristics indicative of the amount and/or type of contamination or deterioration. The analysis results of either embodiment are displayed to a user and/or stored for future use in order to develop a condition history for a fluid in a particular application.

Note that by measuring changes in an oscillator's frequency over a frequency range (to convey impedance information) several assumptions are made. For example, since the present invention is directed, in one aspect, to the monitoring of machine fluids to detect abnormal wear modes or states, a low level concentration of contaminants is assumed. Also, a local linearity for the magnitude of the impedance within the frequency range is assumed. In other words, it is assumed that the frequency range is such that at the frequencies measured, small changes in the impedance of the oil within the frequency range produce linear results.

In addition, although impedance in the present invention is discussed below primarily in conjunction with a real or complex capacitance, impedance can be represented and analyzed in many forms, and each fall within the scope and are contemplated by this invention. For example, the impedance may also be characterized and analyzed by resistance and reactance, capacitance and dissipation factor, admittance, susceptance and conductance. Each of these characterizations have their own terminologies. For example, for capacitance, the terms capacitance, dissipation factor, Tan delta, Q factor or Loss factor may be utilized and are contemplated by this invention.

Referring initially to FIG. 1, a hand-held, portable fluid screening device 10 is shown in accordance with the exemplary embodiments of the invention. The device 10 includes a hand-held sized protective housing 12 having a face 14. A liquid crystal display 16 and a plurality of input and/or operational keys 18 are disposed on the face 14 of the housing 12. A first port 20 included in the housing 12 is configured to receive a capacitive grid or sensor 22 described more fully below in connection with FIGS. 2a and 2b. The sensor 22 has a connector edge 24 for providing an electrical and mechanical connection between the sensor 22 and the circuitry within the housing 12 via the port 20 and a connector 25 within the housing 12 designed to receive the connector edge 24. The sensor 22 includes a cavity 26 for holding a sample of the fluid under test. In addition, the impedance grid or sensor 22 includes a pair of interdigitated electrodes 28 at the bottom of the cavity 26.

A second port 30 is also included in the housing 12. The second port 30 is operable to provide an input/output (I/0) connection between circuitry within the device 10 and an external device as is discussed more fully below. The second port 30 may provide for a conventional hardwired serial port or alternatively may consist of either an RF communication port or an IR communication port, for example.

FIG. 2 is a block diagram of the electronic circuitry included within the fluid screening device 10 in accordance with a first embodiment. The circuitry includes a processor 34 which controls the various operations of the device 10 as described herein. The processor 34 is programmed to control the various components within the device 10 and to perform the calculations discussed herein in order that the condition of the fluid under test can be analyzed. A person having ordinary skill in the art will be able to program the processor 34 using conventional programming techniques based on the various flowcharts and description provided herein. Consequently, additional detail regarding the actual programming has been omitted for sake of brevity.

The processor 34 is coupled to an oscillator circuit 36 via control lines 37a, 37b and an output line 37c. The processor 34 is operable to control various switching operations for the oscillator circuit 36 as described below via control commands provided on lines 37a and 37b and monitors the oscillator circuit output frequency ($f_0$) via line 37c. (It will be appreciated that the term "line" as used herein may also refer to a multi-line bus.) A memory 38 is coupled to the processor 34 via line 39. The memory 38 serves to store the frequency data obtained from the oscillator circuit 36 for processing by the processor 34 and/or subsequent downloading to an external device. The memory 38 includes a non-volatile section for storing the system operating code, data which is to be retained in the memory, etc. The display 16 and the keypad 18 of FIG. 1 are coupled to the processor 34 by lines 40 and 41, respectively. The second port 30, labelled the serial communications port, is a serial communications (e.g., RS-232) I/O port and is also coupled to the processor 34.

In the exemplary embodiment, the processor 34, oscillator circuit 36 and memory 38 have been illustrated as separate components. Alternatively, one or more of these components may be integrated into a single integrated circuit block. Further, although the exemplary embodiment illustrates the memory 38 coupled to the processor 34, the memory 38 alternatively may be partially or completely external to the fluid screening device 10 depending on the amount of information to be stored.

Referring now to FIGS. 2a and 2b, top and side elevation views of the impedance sensor 22 are respectively shown. The sensor 22 includes a dielectric substrate 48 of the type used to produce printed circuit boards, for example. Formed on the substrate 48 is a pair of interdigitated electrodes 28a and 28b. In the preferred embodiment, the electrodes 28a and 28b are patterned generally as an interdigitated square grid array although other patterns (such as a series of interdigitated concentric circles) are certainly possible. The electrodes 28a and 28b are formed on the substrate 48 using conventional printed circuit board techniques, for example.

The substrate 48 includes a card edge tab 50 which is designed to be received by the connector 25. Exposed on the tab 50 are terminals 51a and 51b printed thereon. The terminals 51a and 51b are electrically connected via conductive traces to the electrodes 28a and 28b, respectively. When inserted in the connector 25, the terminals 51a and 51b electrically engage corresponding terminals 52a and 52b which are electrically con nected to the oscillator circuit 36. Thus, the circuit 36 is able to utilize the sensor 22 via the electrodes 28 as a capacitance sensor in establishing an output oscillator frequency.

The sensor 22 further includes a retaining wall 53 formed on top of the substrate 48. The wall 53 forms the cavity 26 about the electrodes 28. The retaining wall 53 is preferably made of inexpensive plastic and is glued, molded or otherwise applied to the substrate 48 in order to form a fluid tight seal therebetween. Consequently, a sample of the fluid under test is poured into the cavity 26 so as to substantially fill the cavity 26 and the retaining wall 53 serves to hold the fluid directly atop the electrodes 28.

Those having ordinary skill in the art will appreciate that the sensor 22 in the exemplary embodiment represents an impedance type sensor. The condition of the fluid such as particulate concentration, oxidation, water content, etc., will have an effect on the dielectric properties of the fluid, and consequently impact the measured impedance of the capacitor formed by the electrodes 28 acting as capacitor plate electrodes within the sensor 22.

Figure 2C:
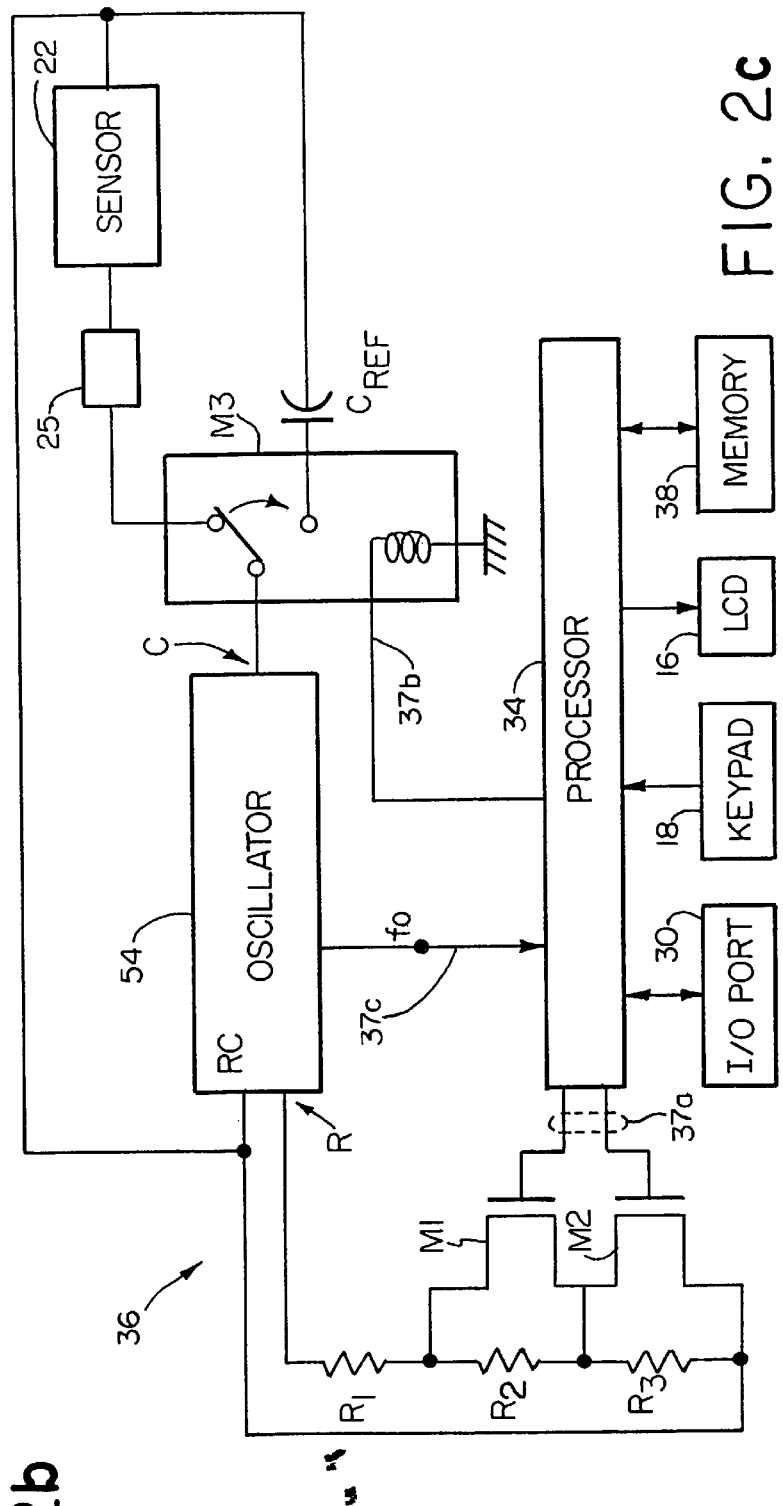
FIG. 2c is a schematic diagram illustrating in greater detail the oscillator and processor circuitry of the embodiment of FIG. 2.

Now turning to FIG. 2c, additional detail is shown with respect to the oscillator circuit 36 of FIG. 2. The processor 34 is coupled to the oscillator circuit 36 via lines 37a–37c. The oscillator circuit 36 includes an oscillator 54 which oscillates at an output frequency that is a function of the values of resistance and capacitance which are input to the oscillator 54. Such an oscillator 54 is well known in the electronics field. The oscillator circuit 36 also includes a bank of resistors $R_1$, $R_2$ and $R_3$, a plurality of switches, M1–M3, and a reference capacitor $C_{REF}$. The resistors $R_1$, $R_2$ and $R_3$ are connected in series between the resistance value input R of the oscillator 54 and an RC common terminal of the oscillator 54. The switches M1 and M2 are connected together in series across the resistors $R_2$ and $R_3$. When switch M1 is on, the effect is that resistor $R_2$ is short circuited effectively from the series combination of resistors $R_1$ and $R_3$. Similarly, when switch M2 is on, the resistor $R_3$ is short circuited from the series combination of resistors $R_1$ and $R_2$. Hence, by controlling the status of the switches M1 and M2 via the control line 37a, various combinations of the resistors $R_1$–$R_3$ can selectively be presented to the oscillator 54. For example, the effective resistance value provided to the R input may be R1, $R_1+R_2$, $R_1+R_2+R_3$ or $R_1+R_3$. As is discussed in more detail below in connection with FIG. 8, the processor 34 controls which combination of resistors $R_1$–$R_3$ are provided to the oscillator 54 in order to determine which particular frequency band (or range) the oscillator 54 will tend to oscillate. By selecting the appropriate values for $R_1$–$R_3$, the oscillator 54 will oscillate at up to four different ranges based on the four possible combinations of the resistors $R_1$–$R_3$. The processor 34 controls the switches M1–M3 (in this exemplary embodiment, the switches are N-channel MOS transistors and a relay, respectively), which thereby alters the effective RC relationship and therefore the output frequency $f_0$ of the oscillator 54 as provided to the processor 34 on line 37c.

The processor 34 also provides control signals via control line 37b to selectively activate the relay switch M3 to selectively couple either the capacitance of the sensor 22 or the capacitance of the reference capacitor $C_{REF}$ to the capacitance input C. For example, when M3 is off, the sensor 22 becomes the effective capacitance for the oscillator 54, and when M3 is on, the reference capacitor $C_{REF}$ becomes the effective capacitance for the oscillator 54 and allows for a calibration functionality of the fluid screening device 10 which will be described in greater detail infra. As is well known by those skilled in the art, the output signal frequency $f_0$ on line 37c is a function of the value of the RC relationship generated by the resistor bank $R_1-R_3$ and one of the capacitances, the sensor 22 or the reference capacitor $C_{REF}$.

The selective combination of resistors $R_1-R_3$ of the resistor bank with either the sensor 22 or the reference capacitor $C_{REF}$ controls the frequency band in which the oscillator 54 oscillates. Preferably, the oscillator output signal frequency $f_0$ is measured in three different frequency bands. Alternatively, however, a larger number of frequency bands can be measured if additional data is desired by adding more resistors to the resistor bank and selectively combining them to achieve a greater number of effective resistances. In this exemplary embodiment, the processor 34 controls whether the fluid sample is analyzed in a low frequency band (e.g., approximately 1 KHz), a middle frequency band (e.g., approximately 10 KHz), or a high frequency band (e.g., approximately 200 KHz). The processor 34 subsequently analyzes the data to determine the presence of various contaminants, particulates, etc. within the fluid based upon the data collected in the various frequency bands. The data can also be compared to similar measurements for a calibration sample, and/or to previous samples of the same oil for purposes of trending.

Thus, according to the present invention, the condition of the fluid under test is determined by analyzing the output signal frequency $f_0$ of the oscillator circuit 36 caused by the impedance/capacitance of the fluid under test over various frequency bands.

An aspect of the invention involves the fluid screening device 10 as a hand-held, portable apparatus. The device 10, in conjunction with the sensor 22, allows a user to easily carry the device 10 to a site (i.e., location) where the fluid is being used. For example, the fluid may be a lubricant used as part of heavy machinery in the field. The sensor 22 allows a user to sample the fluid at the site of the machinery and quickly obtain analysis results without needing to package the sample (which requires special precautions to avoid artificial contamination in packaging), send it to a laboratory, and wait for laboratory analysis results. The device 10 is portable and therefore allows users to avoid the cost and delay associated with shipping fluid samples off-site for analysis. The insertable and removable sensor 22 also advantageously allows a user to utilize the device 10 to analyze various fluids without contamination and/or the need to clean the sensor 22. If a user wishes to sample another, different fluid, the user need only remove the present sensor 22 from the connector 25 and replace it with another. The sensor 22 may be subsequently cleaned at a more convenient time to be used again or may simply be discarded. Due to the inexpensive construction of the sensor 20, it is easy and cost effective simply to dispose of a used sensor 22 and replace it with a new one. Use of the detachable sensor 22 allows the device 10 to promptly analyze, in succession, a diversity of fluids and/or fluids from different sources without the threat of cross-contamination between various fluid samples.

Figure 3:
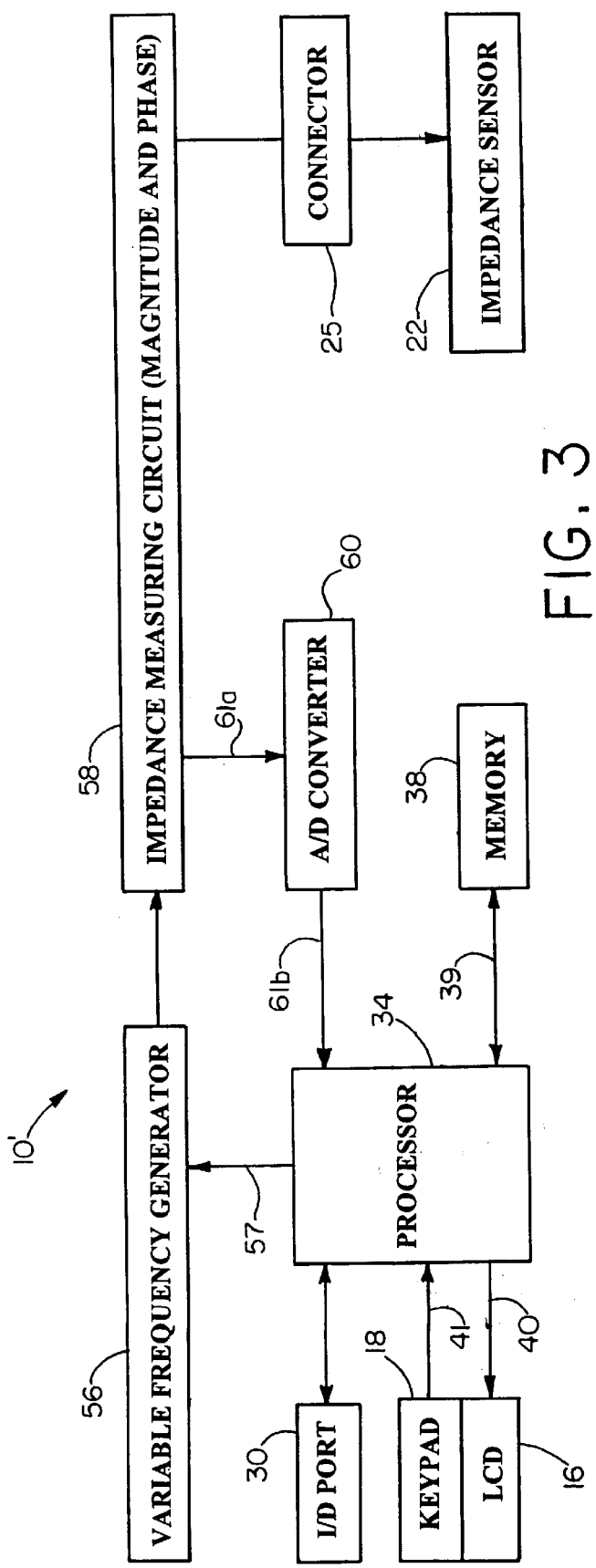
FIG. 3 is a block diagram illustrating a fluid screening device according to a second embodiment of the invention, wherein the device analyzes a complex impedance over a plurality of frequencies to determine a condition of the fluid.

In an alternative embodiment of the portable screening device designated 10', as illustrated in FIG. 3, the processor 34 is coupled to a variable frequency generator 56 via a control line 57. The processor 34 is able to control the output frequency of the variable frequency generator 56 via control commands provided on line 57. An impedance measuring circuit 58 is coupled to the output of the variable frequency generator 56 via line 59. The impedance measuring circuit 58 is of conventional design and is utilized for measuring the magnitude and phase and/or the phase and capacitance of the impedance across two terminals at the signal frequency provided by the variable frequency generator 36 (the "test frequency"). The circuit 58 may include such conventional components as a lock-in amplifier, a bridge circuit, oscillator, etc. The particular design of the circuit 58 is not critical to the invention and can be any conventional design. The terminals across which the circuit 58 measures the impedance are provided in the aforementioned connector 25. As was discussed above in relation to FIGS. 2a and 2b, the connector 25 preferably is a card edge connector for receiving the edge of a substrate included in the sensor 22. A user can easily insert and remove the sensor 22 from the connector 25 by simply pulling or pushing the card edge tab 50 from/into the connector 25. The interdigitated electrodes 28 of the sensor 22 are coupled to the terminals of the impedance measuring circuit 58 by way of the connector 25.

An analog-to-digital converter (A/D) 60 is coupled between the impedance measuring circuit 58 (and/or phase and capacitance) and the processor 34 via lines 61a and 61b. The circuit 58 provides analog information to the A/D 60 via line 61a indicative of the magnitude and phase of the impedance across the sensor 22 at the test signal frequency. The A/D 60 converts the magnitude and phase values to digital signals which are input to the processor 34 via line 61b.

As in the previous embodiment, the memory 38 is coupled to the processor 34 via line 39. The memory 38 serves to store the impedance data obtained from the circuit 58 for processing by the processor 34 and/or subsequent downloading to an external device. The memory 38 includes a non-volatile section for storing the system operating code, data which is to be retained in the memory, etc. The display 16 and the keypad 18 of FIG. 1 are coupled to the processor 34 by lines 40 and 41, respectively. The second port 30 is a serial (e.g., RS-232) I/O port and is also coupled to the processor 34.

In this alternative embodiment, the processor 34, the variable frequency generator 56, the impedance measuring circuit 58 and the A/D converter 60 have all been illustrated as separate components. Alternatively, however, one or more of these components may also be integrated into a single circuit block. Further, although the exemplary embodiment illustrates the memory 38 coupled to the processor 34, the memory 38 alternatively may be partially or completely external to the fluid screening device 10' depending on the amount of information to be stored.

Figure 5:
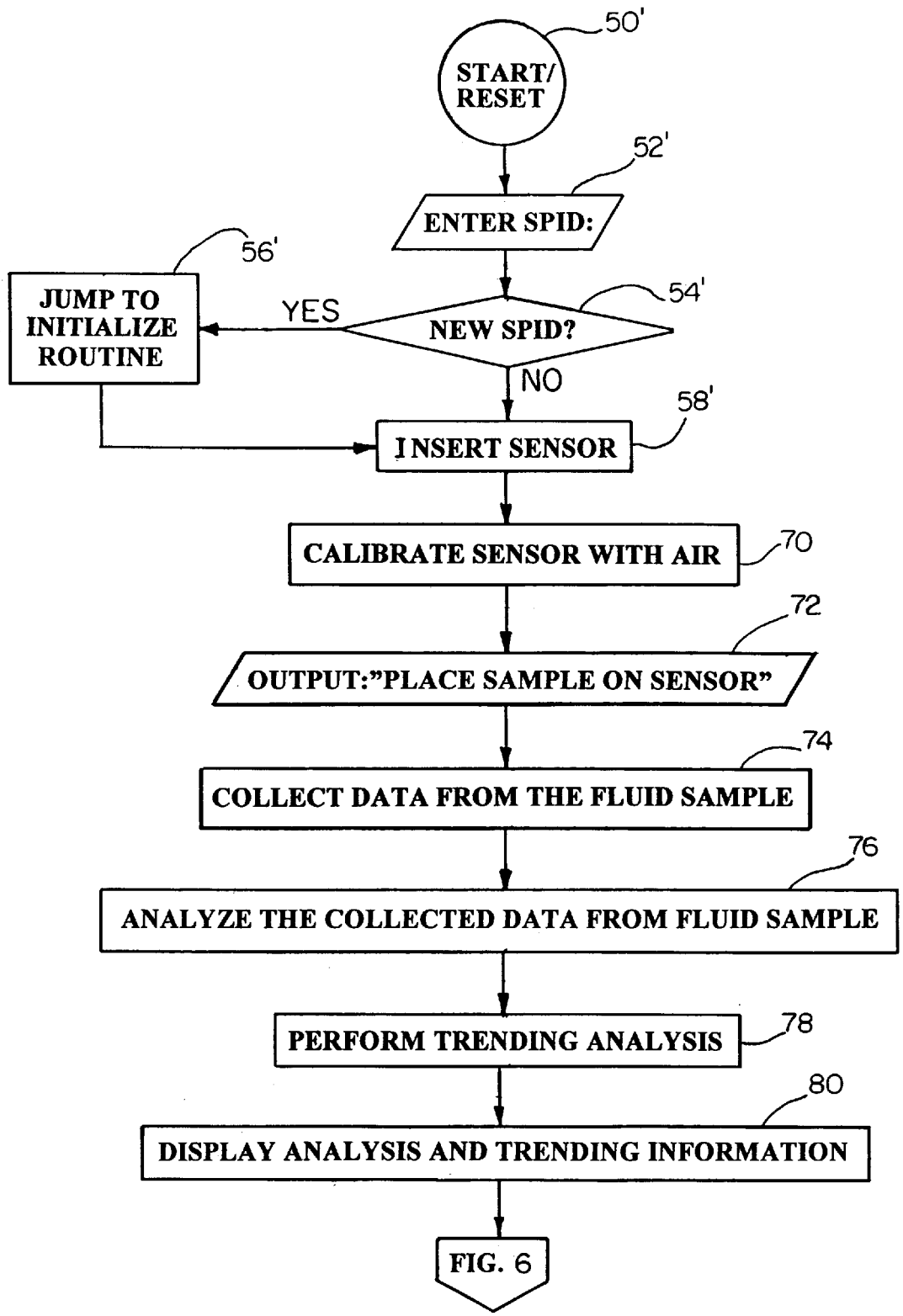
FIGS. 5 and 6 show a flowchart illustrating the overall operation of the fluid screening device in accordance with the present invention.

A functional description of the first embodiment of the invention (as illustrated in FIGS. 1 and 2) will now follow. FIG. 5 illustrates a flowchart diagram which shows the general operation of the exemplary fluid screening device 10 to analyze the condition of fluid samples. In this exemplary embodiment, the device 10 analyzes fluids utilized as lubricants in industrial applications. Alternatively, other fluids for various applications may be analyzed with the fluid screening device 10. The operation of the fluid screening device 10 begins with start/reset step 50' in response to a user input on the key pad 18 (such as pressing a "Power On" key, for example). At step 52', the processor 34 prompts the user via the display 16 to enter an identification number or name ("SPID") which is to be associated with the current fluid under test. The user may input such SPID information using the keypad 18. The processor 34 then proceeds to associate the SPID with all data subsequently obtained from the sample together with adding a time stamp to the data when obtained. The processor 34 also stores in memory 38 a list of all SPIDs for which it has data stored. In step 54', the processor 34 compares the SPID entered in step 52' with the list of SPIDs in the memory 38 to determine if the fluid is a new fluid not previously tested, or whether this is the second, third or nth sample of this particular fluid. If the response to the inquiry at step 54' is yes, the fluid screening device 10 then begins an initialization routine at step 56' in which a file is created in memory 38 for that particular fluid.

Figure 7:
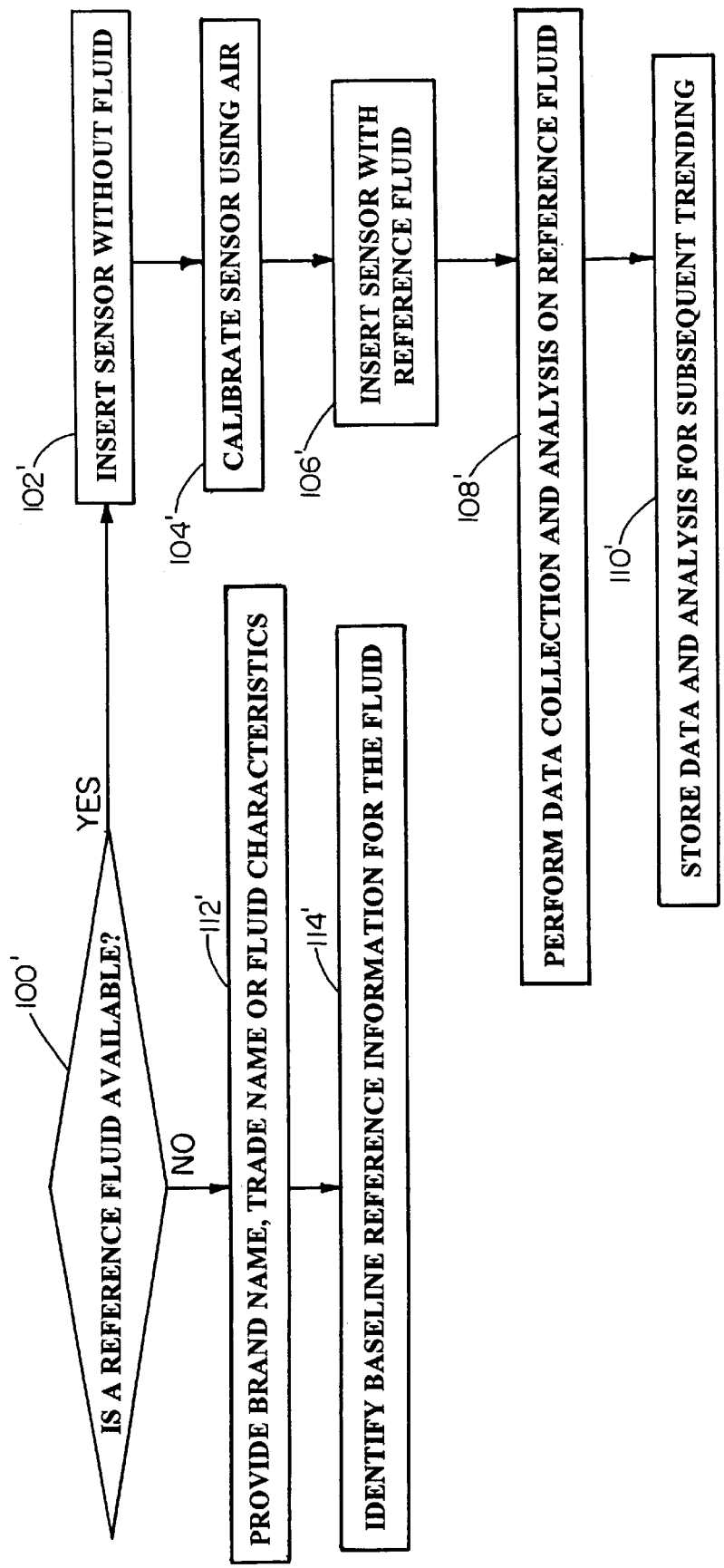
FIG. 7 is a flowchart illustrating an initialization routine utilized prior to collecting data from a fluid sample.

The initialization routine is illustrated in detail in FIG. 7. The goal of the initialization routine is to obtain reference data for the particular fluid to be analyzed. Alternatively, if no reference fluid is available, the initialization routine queries the user regarding the type or make of fluid being tested so that the processor may select reference baseline data that is stored in the memory 38 or an external memory.

During initialization the user is asked whether a reference fluid is available at step 100' of FIG. 7. If the user indicates that a reference fluid is available, the processor 34 requests insertion of the sensor (capacitive grid) without the fluid at step 102' to perform an initial calibration of the sensor using air as the capacitor dielectric material. The output signal frequencies of the oscillator 54 are stored in the memory 38 using both the sensor 22 and the reference capacitor $C_{REF}$ iteratively and the data is used for calibration of the present sensor 22 being used (step 104'). The processor 34 then requests via the display 16 that the reference fluid be submitted at step 106'. The user, in response, pours the reference fluid into the cavity 26 of the sensor 22. The reference fluid is then analyzed via the data collection and analysis routines of FIGS. 8, 12 and 13 (step 108') which will be described infra. At step 110' the reference data for the reference fluid is stored in the memory 38 for use in subsequent analysis.

If the user indicates that no reference fluid is available at step 100', the processor 34 will query the user at step 112' via the display 16 regarding the type, brand name or tradename of the fluid to be tested. Using this information, the processor at step 114' is programmed to identify baseline reference information for the fluid or information that most closely approximates the fluid (i.e., virtual reference information). This baseline information is then identified and retrieved from the memory 38 for subsequent analysis and trending operations. After initialization, the processor 34 proceeds to step 58' of FIG. 5 in which it prompts the user via the display 16 to insert a new impedance sensor 22 into the connector 25 for use with the fluid under test.

If in step 54' of FIG. 5, the processor 34 determines that the SPID entered in step 52' corresponds to a SPID stored in the memory 38, it is assumed that the fluid under test is a subsequent sample of a fluid which was previously screened. Since the device 10 has already been initialized for such a fluid, the processor 34 goes directly to step 58' where it requests that the sensor 22 be coupled to the connector 25. The device 10 preferably automatically detects the coupling of the impedance sensor 22 into the first port 20, and specifically the connector 25. The coupling of impedance sensor 22 to the connector 25 can be detected as a sudden change in the impedance across terminals 52a and 52b as measured by the output frequency of the oscillator circuit 36.

The processor 34 proceeds to calibrate the impedance sensor 22 with respect to air (i.e., absent any fluid in the cavity 26) according to a calibration routine at step 70 of FIG. 5. Specifically, the processor 34 switches the switch M3 between the sensor 22 and the reference capacitor $C_{REF}$ which will have a known value. Hence, when the reference capacitor $C_{REF}$ is selected, the output frequency $f_0$ of the oscillator is a known frequency. Any variance from such known frequency when M3 has coupled the sensor 22 to the circuit 36 is detected by the processor 34 and is attributed to system measurement error. The processor 34 can then account for such error by appropriate scaling of the output frequency obtained using the sensor 22.

Following step 70, the user at step 72 is prompted by the processor 34 via the display 16 to place a fluid sample into the cavity 26 of the sensor 22. Upon insertion of the sensor 22 containing the fluid for test, there will be a relatively sudden and large change in the output frequency $f_0$ from the oscillator 54 due to a relatively large change in the effective capacitance of the sensor 22. The processor 34 detects such relative change and initiates a predetermined timeout period prior to beginning its actual analysis of the output from the oscillator 54. The processor 34 is programmed to wait the predetermined period of time such that each fluid sample will be analyzed at approximately the same time following insertion into the sensor 22 for consistency. Preferably, the predetermined time is less than or equal to about 30 seconds. Alternatively, the predetermined wait time may be extended to, for example, 45 seconds or longer.

Figure 8:
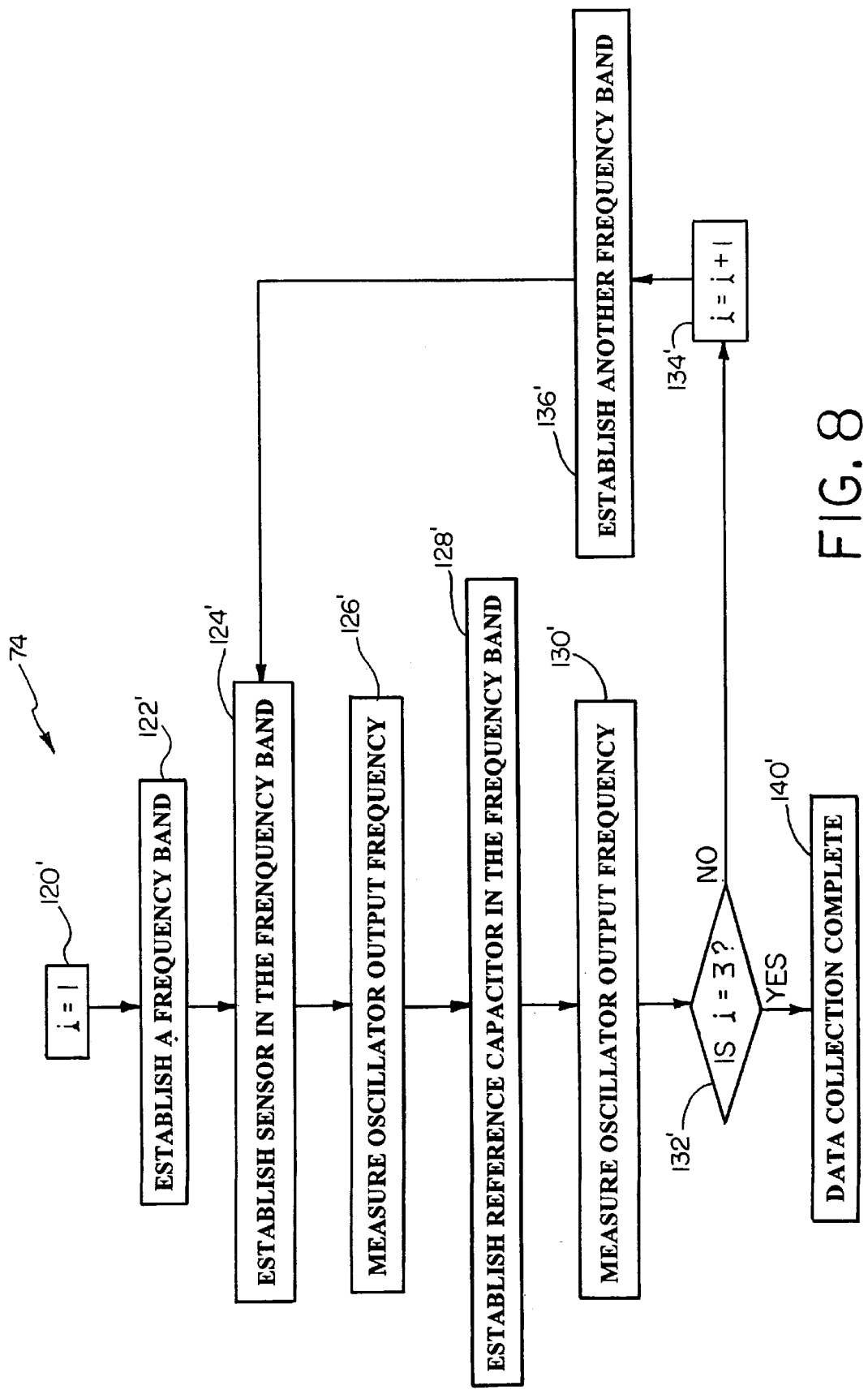
FIG. 8 is a detailed flowchart illustrating the step of collecting data from a fluid sample in accordance with the first embodiment of the present invention.

The device 10 then collects impedance data from the fluid sample at step 74 as described more fully below in relation to FIG. 8. Following step 74, the processor 34 proceeds to step 76 in which it analyzes the collected data as discussed more fully below. After step 76, the processor 34 proceeds to step 78 in which it executes an optional trending routine by comparing the results of the current sample with the previous sample of the same fluid. Next, in step 80 the processor 34 displays the results of the fluid condition analysis and any trending information on the display 16 and stores the results in the memory 38.

Figure 6:
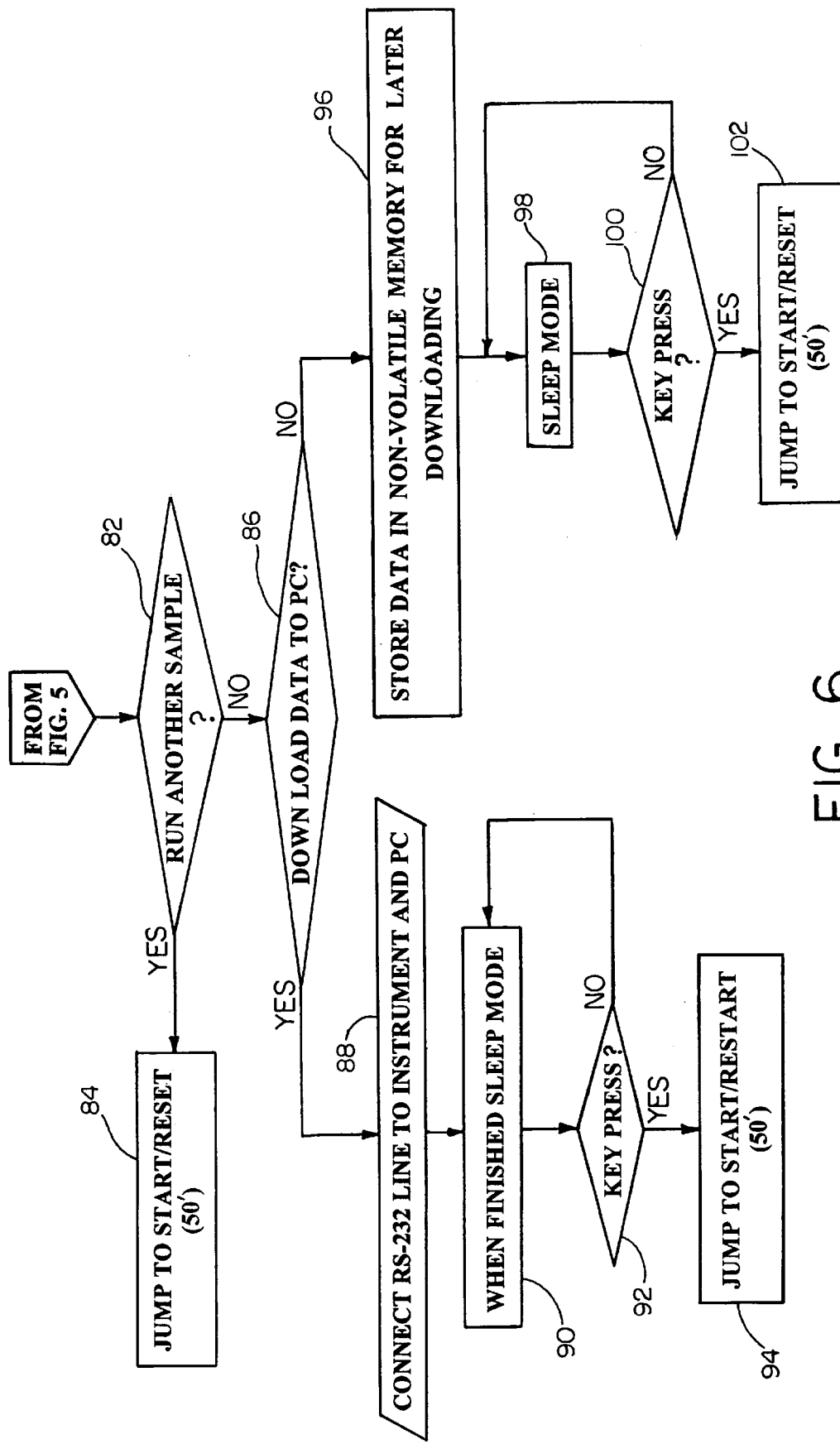

FIG. 6 is a flowchart diagram illustrating the continued operation of the processor 34. Following step 80, the processor 34 in step 82 queries the user via display 16 whether the user wants to run another sample. If the user responds 'yes' via an input on the keypad 18 or the like, the processor 34 returns to the start or reset step 50' of FIG. 5. The step of returning to step 50' is represented as step 84 of FIG. 6. If the user at step 82 chooses to discontinue analyzing fluid samples by responding 'no' in step 82 via an input on the keypad 18, the processor 34 proceeds to step 86 in which it queries via the display 16 whether the user wishes to down-load the collected and analyzed data to an external device such as a personal computer. If the user responds 'yes' via a keypad input on the keypad 18, for example, the processor 34 then displays a prompt in step 88 instructing the user to connect the I/O port 30 to the external device via an RS-232 line or the like. Using any conventional predefined protocol, the data collected by the device 10 is then downloaded to the external device. Upon completion of data transfer at step 88, the processor 34 proceeds to step 90 in which it places the device 10 into a sleep mode, thereby saving power. If the user wishes to utilize the fluid screening device 10 again, the user may simply press any key 18 at step 92, at which point the processor 34 detects such action and proceeds to jump to the start/reset step 50' of FIG. 5. Otherwise, the processor 34 continues to loop through steps 90 and 92 and remains in the sleep mode.

If the user, upon being queried in step 86 whether he or she wishes to download data to an external device, answers in the negative, the processor 34 will proceed to step 96 and store the data obtained from the sample in a non-volatile portion of the memory 38. In this manner, the data is saved for subsequent downloading. The processor 34 then enters the device 10 into the sleep mode at step 98, at which time it will remain in that state until someone wishes to use the fluid screening device 10 again. At that time, one simply presses any key 18 at step 100 which returns the processor 34 back to step 50' of FIG. 5.

At step 74 in FIG. 5, the fluid screening device 10 collects data from the fluid sample within the sensor. The manner in which the data is collected is illustrated in the flowchart of FIG. 8. At step 120', a variable labelled "i" is assigned a value 1 and the variable is monitored by the processor 34. A frequency band is established at step 122', wherein the processor 34, via the control line 37a, selectively couples one or more of the resistors $R_1$–$R_3$ in the resistor bank to the R input of the oscillator 54. The first selected frequency band may be the high frequency band of approximately 200 KHz. Alternatively, the first selected frequency may be any of the frequency bands as desired. The sensor 22 is established in the high frequency band at step 124', wherein the processor 34 via the control line 37b ensures that M3 is off to thereby couple the sensor 22 to the oscillator 54. The RC relationship caused by the effective resistance of the resistor bank and the capacitance of the fluid sample in the sensor 22 dictates an output oscillation frequency $f_0$ of the oscillator 54 which is measured and stored by the processor 34 at step 126'. The processor 34 then establishes the reference capacitor $C_{REF}$ in the established frequency band in step 128' by activating the relay M3. As a result, $C_{REF}$ dictates an output oscillation frequency $f_0$ of the oscillator 54 which is measured and stored by the processor 34 at step 130'. The processor 34 then checks to see whether the variable "i" is equal to three (3) at step 132', and if not, increments the variable "i" at step 134'. At step 136', another frequency band is established by the processor 34 by selectively coupling resistors $R_1$–$R_3$ in the resistor bank using the transistors M1 and M2 via control line 37a. Preferably, the second frequency band is a middle frequency band of approximately 10 KHz. Steps 124' to 136' are then repeated at the middle frequency and then at a low frequency band of approximately 1 KHz and at step 132', "i" is then equal to three (3) and the data collection is discontinued (step 140').

Once data collection is complete at step 140', six (6) pieces of data exist: oscillator output frequencies in three frequency bands, wherein three data points reflect the sensor 22 as the oscillator circuit capacitor and the other three data points reflect the reference capacitor $C_{REF}$ as the oscillator circuit capacitor.

Figure 9:
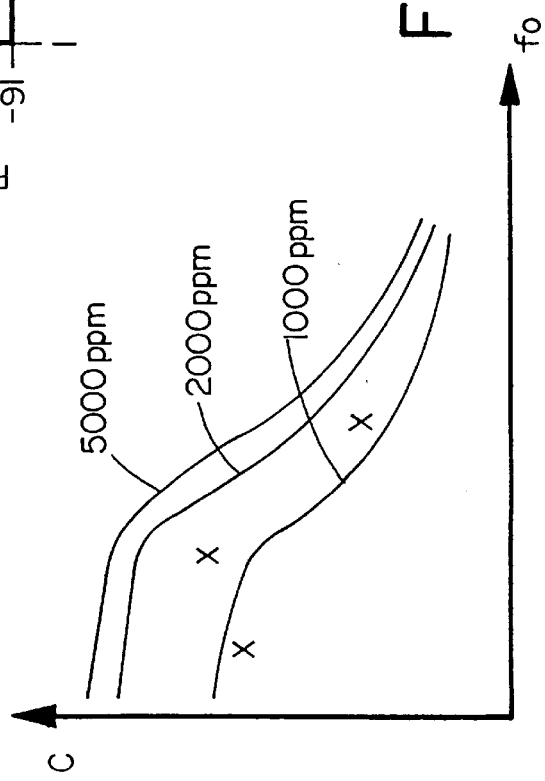
FIG. 9 is a graph illustrating the measured frequency of an oscillator circuit in three frequency bands to predict fluid contamination levels.

As discussed earlier, the output frequency of the oscillator circuit 36 can be expressed as a function of the effective resistance of the resistor bank and the capacitance of the sensor 22. Since the effective resistance is known and the frequency has been measured, the capacitance value of the sensor 22 containing the fluid can be calculated at the three different frequencies. These data points may then be plotted as illustrated in FIG. 9 and compared with known curves to identify contamination in the fluid sample. The corresponding frequency values obtained from the reference capacitor can be used to compensate for any errors which may have been introduced due to temperature, etc. The change in capacitance characteristic over frequency for the fluid under test is then utilized to identify contamination in the fluid.

More specifically, in step 76 (FIG. 5) the data is analyzed in order to obtain such information as the existence of particulate or oxidation in the fluid under test. For example, if a relatively constant change in the measured capacitance occurs at all frequencies for a given lubricant-type fluid when compared to a baseline reference, this may indicate the presence of particulates or oxidation. Alternatively, a very large change in the measured capacitance at only the low frequency relative to a baseline reference can be indicative of water contamination in a lubricant-type fluid. Based on known characteristics of the types of fluid under test, the capacitance measurements across different frequencies as obtained by the device 10 may be used to perform an analysis as to the condition of the fluid. The processor 34 may be programmed to perform such analysis in step 76 (FIG. 5) and display the results or the data may be evaluated by an external computer as previously discussed.

Trending is performed in step 78 as represented in FIG. 5. Such trending may include comparing the data obtained in step 74 with data obtained from the same fluid under test during previously conducted analyses.

In this exemplary embodiment, only three data points were taken for each sample. It should be evident, however, that a greater number of data points may also be taken by adding resistors to the resistor bank to establish a larger number of frequency bands. This provides greater curve resolution if needed.

The device 10 may use a single oscillator circuit 36 to collect the data at three or more frequencies. Alternatively, the device 10 may collect multiple data points by using multiple oscillator circuits wherein each circuit would utilize the sensor 22 as the effective capacitor. In this manner, all the desired data points would be obtained simultaneously or substantially simultaneously.

In addition, the reference capacitor $C_{REF}$ provides reference data points for a known capacitance. Therefore, use of the reference capacitor, although not mandatory, allows for error correction and calibration functionality of the oscillator circuit 36.

The fluid screening device 10, as illustrated through the system operation of FIGS. 5 and 6, provides various advantageous features. The fluid contaminant analyzer 10 allows a user to enter a new sample at steps 54' and 56' and collect data, or to sample the same fluid over a period of time and build up a history profile of a particular fluid through step 78. Step 52' advantageously allows a user to identify his or her sample by number or name in order to keep the collected and analyzed data distinct. The trending routine at step 78 (which will be described in greater detail infra) allows a user to manipulate the collected and analyzed data. Further, the device 10 also advantageously allows a user to run multiple samples iteratively. Step 82 of FIG. 6 allows a user to dispose of a first impedance sensor 22 and insert a new sample of a fluid into the cavity 26 of a second unused impedance sensor 22. The device 10 also allows a user to download the collected and analyzed data to an external device at steps 86 and 88. This feature allows a user to analyze or manipulate the collected and analyzed data further using other analysis techniques. The device 10 also provides a sleep mode at step 90 and step 98 to save power and thereby increase battery life of the device 10.

Figure 4:
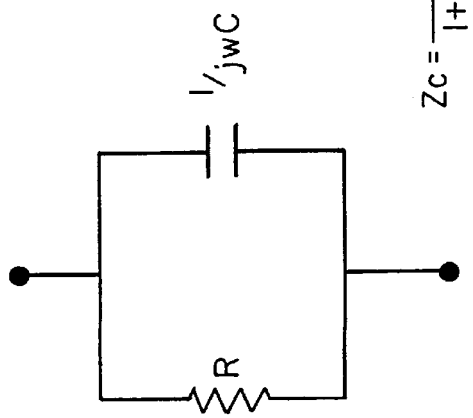
FIG. 4 is a schematic diagram illustrating an equivalent circuit model for a non-ideal capacitor.

In the second embodiment of the invention described above in connection with FIG. 3, the fluid screening device 10' utilizes a non-ideal capacitor model to obtain impedance information regarding the condition of a fluid under test. An ideal capacitor is lossless. In an ideal state, a capacitor stores energy without any loss due to leakage of current, etc. Non-ideal capacitors, however, do not behave as open circuits, but rather exhibit some conductance of the dielectric, leakage, etc. A non-ideal capacitor may be therefore modeled, as illustrated in FIG. 4, as a resistance (R) in parallel with a capacitance (C). In this manner, a capacitor may be properly viewed as having a complex impedance. The complex impedance may be expressed as: $Z_c = R/(1+j\omega CR)$, where $Z_c$ has a real component and an imaginary component. Please note that although the second embodiment is discussed in conjunction with utilization of a complex impedance, the first embodiment may also incorporate and utilize the complex impedance of a non-ideal capacitor.

An uncontaminated fluid will have a complex impedance response across a range of frequencies which is unique for that particular fluid. This is evident in looking at the complex impedance model above where the imaginary component is a function of $\omega$ which is $2\pi f$, wherein f represents the frequency in Hz. A contaminated fluid, due to its particulate impurities or breakdown via oxidation, for example, will diverge from its uncontaminated counterpart in its complex impedance response across the range of frequencies. By separating the amplitude and phase of the complex impedance of the contaminated fluid and comparing it with expected values based upon a corresponding uncontaminated fluid (see FIGS. 10a and 10b), one can identify the existence of particulate contaminants or oxidation and further identify the contamination substance and its level of contamination.

A substantial amount of information regarding particulate contamination may be gleaned at lower frequencies by analyzing the conductivity of the dielectric of the capacitor. Particulate contaminants such as soot or metals have conductivities which are generally higher than most fluids. Other contaminants such as water are also generally more conductive than other fluids (particularly those being utilized as lubricants in industrial applications). By measuring the amplitude of the complex impedance at low frequencies (which is dominated by the conductivity of the dielectric) and comparing the amplitude to predetermined values corresponding to uncontaminated fluids, one may determine whether particulate contamination exists in the fluid as illustrated by the baseline fluid curve 250 and the fluid under test curve 252 in FIG. 10b.

Figure 10A:
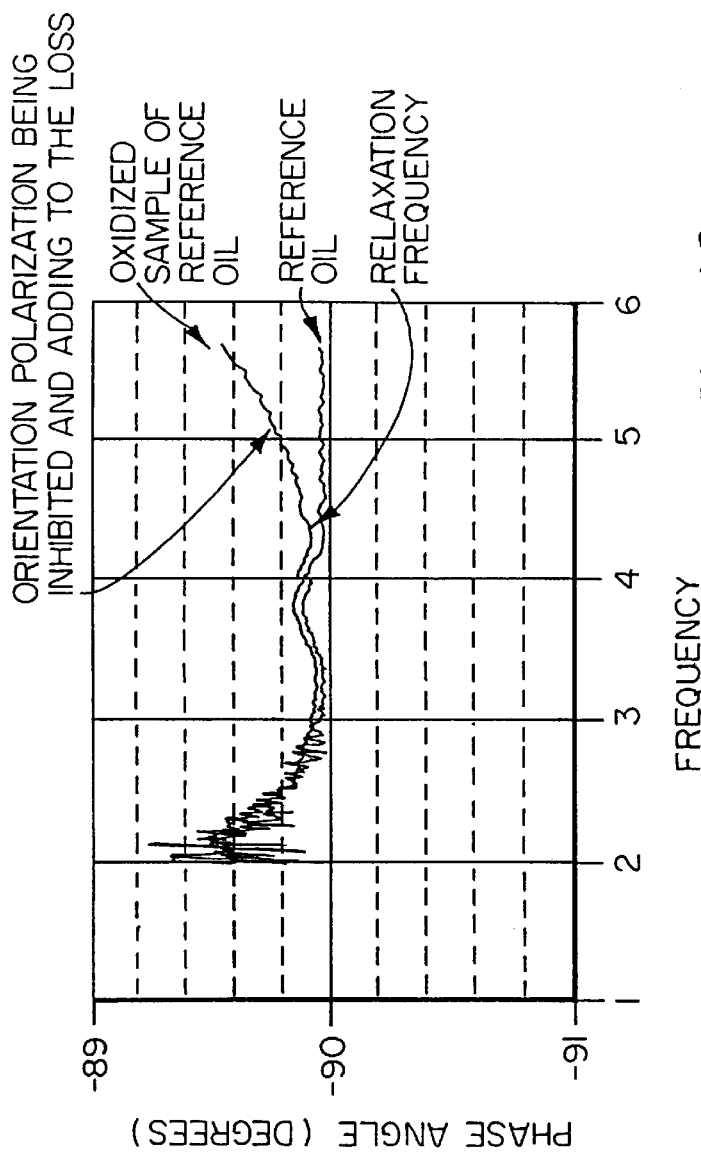
FIG. 10a is a graph illustrating the phase of the complex impedance of two fluid samples with respect to frequency, one sample being an uncontaminated fluid and the other being a contaminated fluid.

Metallic particulate contaminants from machine wear and lubricant deterioration due to oxidation may be detected more readily through a higher range of frequencies by indirectly evaluating the permittivity of the fluid. The permittivity of a fluid describes how the fluid responds in an electric field. When a fluid breaks down, experiencing oxidation, it is hypothesized that the hydrocarbon chains in the molecular structure split and form polar dipoles. Therefore, under the influence of an electric field, the dipoles will become oriented in the direction of the electric field. When the electric field changes its direction, the dipoles also re-orient themselves with the changing field. As the frequency escalates, it becomes more difficult for the dipoles to keep pace with the field variations. The maximum frequency at which the dipoles can keep up with changing electric fields is called the relaxation frequency. At frequencies greater than the relaxation frequency the dipole alignment with the changing electric field lags, causing a dropoff in the phase of the complex impedance as illustrated in FIG. 10a. In this manner, one may indirectly evaluate the permittivity of the fluid by measuring the complex impedance of the fluid across a frequency range. Ferromagnetic particulates may also be detected more readily at a higher range of frequencies due to their behavior in electric fields.

Figures 10B, 11:
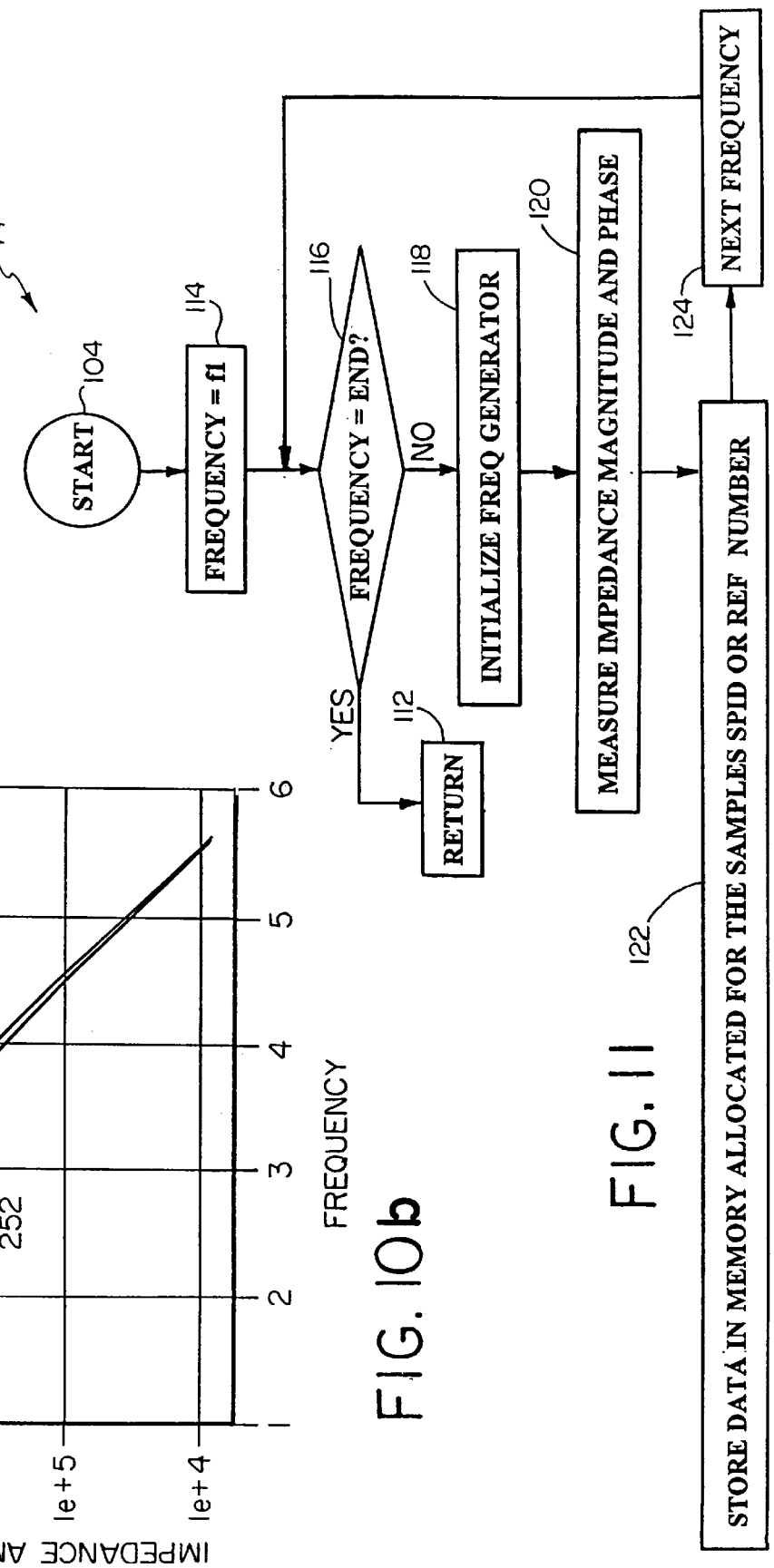
FIG. 10b is a graph illustrating the magnitude of the complex impedance of the two fluid samples with respect to frequency, one sample being an uncontaminated fluid and the other being a contaminated fluid.
FIG. 11 is a detailed flowchart illustrating the step of collecting data from a fluid sample according to the second embodiment of the invention.

Note that FIGS. 10a and 10b are not necessarily related to one another, but rather exist to illustrate how the complex impedance, both magnitude and phase, may be utilized to make determinations regarding the amount and type of contamination within a fluid.

The second embodiment of FIG. 3 differs from the first embodiment of FIG. 2 primarily in the manner in which data is collected and analyzed (steps 74 and 76 of FIG. 5). Otherwise, the analysis routine of FIGS. 5 and 6 is substantially the same for both embodiments. Step 74 of the data collection routine of the second embodiment is illustrated in detail in the flowchart of FIG. 11. Step 74 begins at the start step 104 and proceeds to step 114 where a frequency sweep is initiated by the processor 34.

Specifically, at step 114 the initial frequency for the frequency sweep is reset to $f_1$ (which may be DC or 0Hz). The processor 34 then determines at step 116 whether the current frequency is at a predefined end of the frequency sweep band. If it is not, the variable frequency generator 56 is initialized at step 118 in order that the output of the generator 56 is equal to the frequency. At step 120 which follows step 118, the output of the variable frequency generator 56 serves via the circuit 58 as an excitation signal to the sensor 22 and the complex impedance of the sensor 22 is measured by the impedance measuring circuit 58. The complex impedance is measured in terms of its magnitude and phase according to conventional techniques. The magnitude and phase data for that particular frequency is stored in the memory 38 at step 122.

At step 124, the frequency is incremented to the next frequency in the frequency range. In the preferred embodiment, the frequency band across which the impedance is measured is DC to 50 MHz. The band is divided in M equal frequency increments and in step 124 the output frequency of the generator 56 is incremented by one increment. Although the increments may be equal, they need not be, but rather may be customized if useful data is centered at various frequencies. Following step 124 processor 34 loops back to step 116 where again the processor 34 determines whether the frequency (which has now been incremented) has reached the end of the frequency range. If not, the steps of adjusting the output of the generator 56 in accordance with the current value of frequency, measuring the impedance magnitude and phase and storing that data in the memory 38 are repeated (steps 118, 120, 122). The frequency is then incremented in step 124 to the next frequency in the frequency range and the steps 116, 118, 120 and 122 are continued until at step 116 the frequency has reached the end of the frequency range. When the variable frequency generator 36 has swept through the its entire predefined frequency range and impedance values are obtained as determined at step 116, the processor 34 will determine that the frequency sweep is complete and will return to step 76 of FIG. 5 (see step 112 in FIG. 11).

The processor 34 may be programmed to calculate and store the average impedance at each of the respective frequencies throughout the band in addition to storing the data for each individual sweep. In an exemplary embodiment, the processor 34 automatically selects the frequency range to be swept for the data collection step 74.

Figure 12:
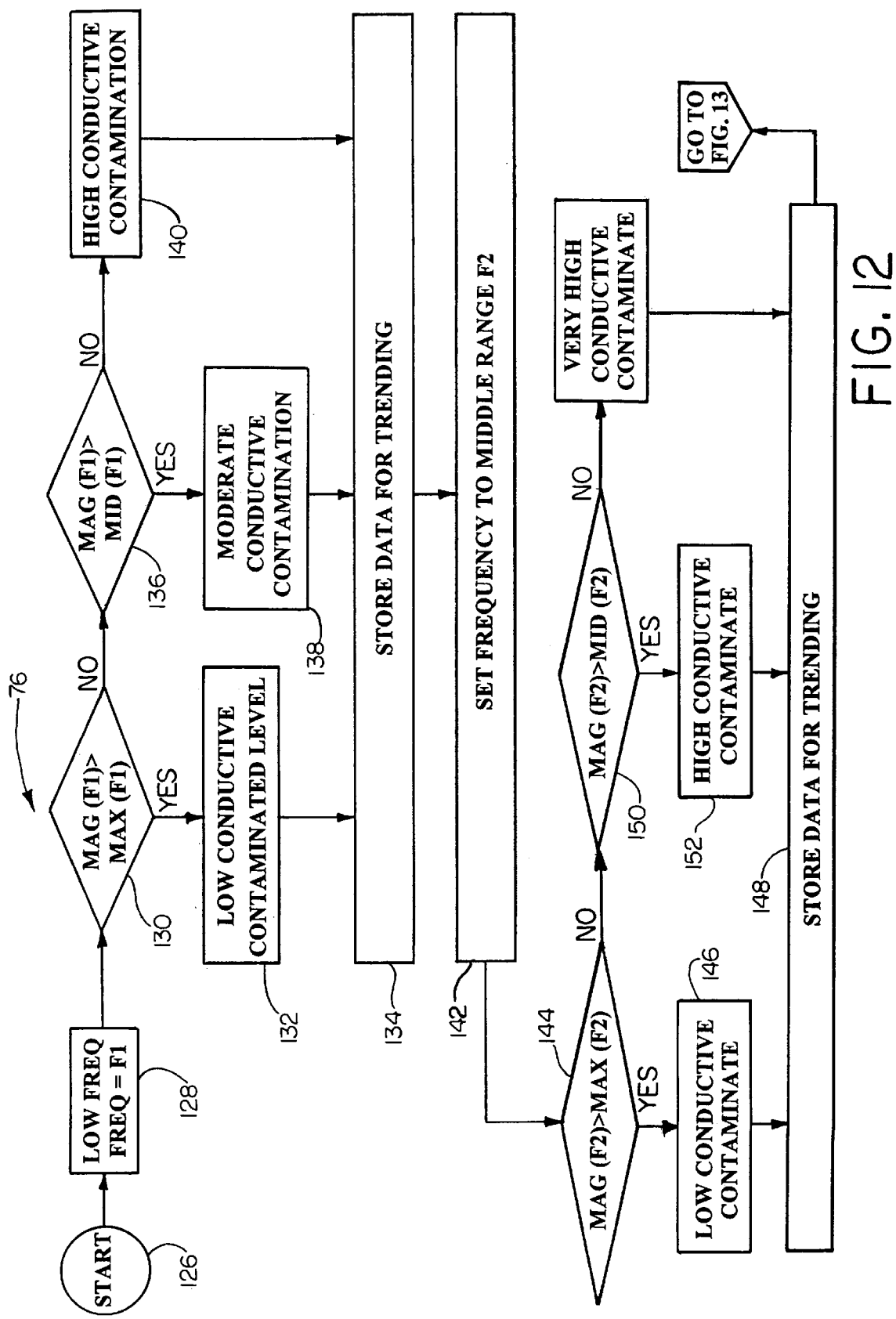
FIGS. 12 and 13 are a detailed flowchart illustrating a routine for analyzing the data collected from the fluid sample in accordance with the second embodiment of the invention.
Figure 13:
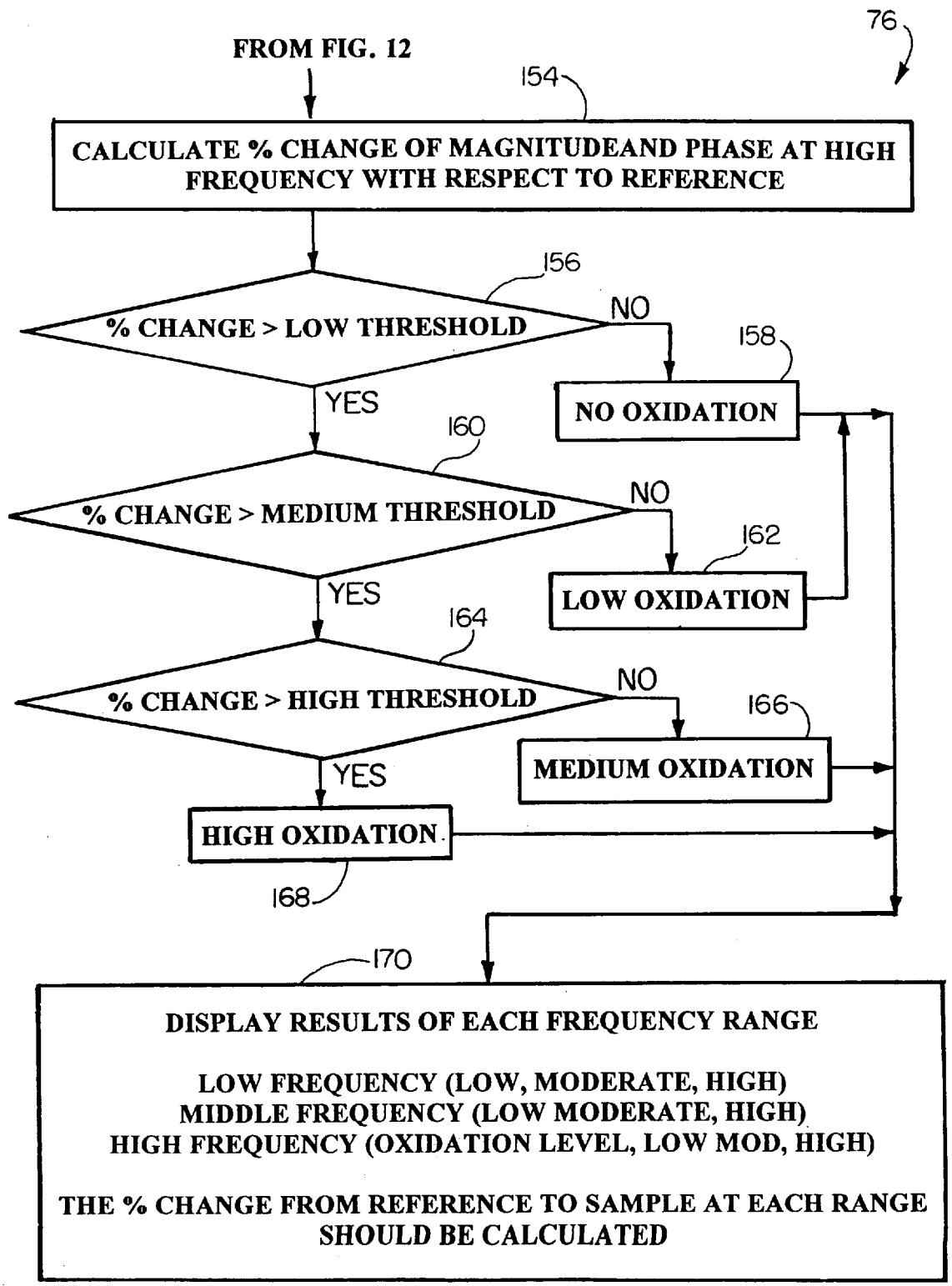

FIGS. 12 and 13 represent a detailed flowchart illustrating the particular analysis routine according to the second embodiment for analyzing the impedance data as represented in step 76 of FIG. 5.

At step 128, the processor 34 identifies a low frequency signal datapoint (F1) from the collected data of step 74. The processor 34 then compares the impedance magnitude with a first predetermined value (Max (F1)) at step 130. If the impedance magnitude exceeds the first predetermined value, the processor 34 determines that a low conductive contaminate level exists in the fluid sample (Step 132) which may be communicated to the user via the LCD display 16 or the I/O port 30 to an external computer or display device. In addition, both the impedance magnitude and the contaminate level conclusion may be saved via the processor 34 in the memory 38 for trending analysis at step 134.

If the impedance magnitude does not exceed the first predetermined value (Max (F1)), the processor 34 compares the impedance magnitude with a second predetermined value (Mid (F1)) at step 136. If the impedance magnitude exceeds the second predetermined value (that is, Mid (F1) <Z<Max (F1)), the processor 34 determines that a moderate conductive contamination level exists in the fluid sample (step 138). This determination may then be communicated via the processor 34 to the user through either the LCD display 16 or the I/O part 30. Further, the processor 34 may save both the impedance magnitude and the contamination level conclusion in the memory 38 for trending analysis at step 134.

If the impedance magnitude at the first frequency (F1) does not exceed the second threshold value (Mid (F1)), a high conductive contamination determination is made by the processor 34 at step 140 and communicated to the user via either the LCD 16 or the I/O part 30. In addition, the processor 34 stores the impedance magnitude and the contamination determination in the memory 38 for tending purposes at step 134 and then proceeds to another frequency at step 142.

At step 142, the processor 34 identifies a mid-level frequency signal datapoint (F2) from the collected data of step 74. The processor 34 compares the impedance magnitude with a third predetermined value (Max (F2)) at step 144. If the impedance magnitude exceeds Max (F2), the processor 34 determines that a low level conductive contaminant exists in the fluid sample (step 146) and is communicated to the user via either the LCD display 16 or the I/O part 30. Both the impedance magnitude measurement and the contamination determination is saved by the processor 34 in the memory for subsequent trending analysis at step 148.

If the impedance magnitude does not exceed Max (F2), the processor 34 compares the impedance magnitude with a fourth predetermined value (Mid (F2)) at step 150. If the impedance magnitude exceeds this value (Mid (F2)<Z<Max (F2)), the processor 34 determines that a high conductive contamination level exists in the fluid sample (step 152).

This determination is communicated to the user by the processor 34 vis either the LCD display 16 or the I/O port 30 and is subsequently stored in the memory 38 for trending analysis at step 148.

If the impedance magnitude at the second frequency (F2) does not exceed Mid (F2), a very high conductive contamination determination is made by the processor 34 at step 154 and both the impedance magnitude and the contamination determination are saved in the memory 38 for trending analysis at step 148.

The analysis routine 76 continues and is further illustrated in FIG. 13. At step 154, the processor 34 identifies a high frequency signal datapoint from the collected data of step 74. The processor 34 then calculates the percentage change in both the impedance magnitude and phase between the reference fluid and the fluid under test at step 154.

After calculating the percentage change fo the magnitude and phase of the test fluid with the reference fluid, the processor 34 compares the impedance magnitude percentage change with a first (or low) percentage change threshold at step 156. If the calculated percentage change does not exceed the first percentage threshold, the processor 34 makes a determination that no oxidation of the sample fluid has occurred at step 158. Similarly, the processor 34 compares the phase of the impedance to a first phase threshold value. The processor 34 communicates the determination to the user via the LCD display 16 or the I/O port 30.

If the calculated percentage exceeds the first percentage thresholds, the processor 34 compares the calculated percentage change of the impedance magnitude and phase to a pair of second (or medium) percentage change thresholds (for impedance magnitude and phase respectively) at step 160. If the calculated percentage change does not exceed the medium threshold (that is, low threshold <X<medium threshold) the processor 34 makes a determination that a low oxidation condition exists (step 162) in the fluid sample and communicates this result to the user via the LCD display 16 or alternatively the I/O port 30.

Lastly, if the calculated percentage change for the magnitude and phase exceeds the medium thresholds at step 160, the processor 34 compares the calculated percentage change to a pair of third (or high) percentage thresholds for the magnitude and phase, respectively, at step 164. If the calculated percentage changes do not exceed the high thresholds (medium threshold <X<high threshold), the processor 34 determines that a medium oxidation condition exists in the fluid sample at step 166. Conversely, if the calculated percentage changes do exceed the high threshold, the processor 34 determines that a high oxidation condition exists in the fluid sample at step 168.

Other information in the frequency spectrum may also be utilized in the analysis routine. For example, the resonance of the grid could be easily extracted by the magnitude and phase measurements across the range of frequencies.

Figure 14:
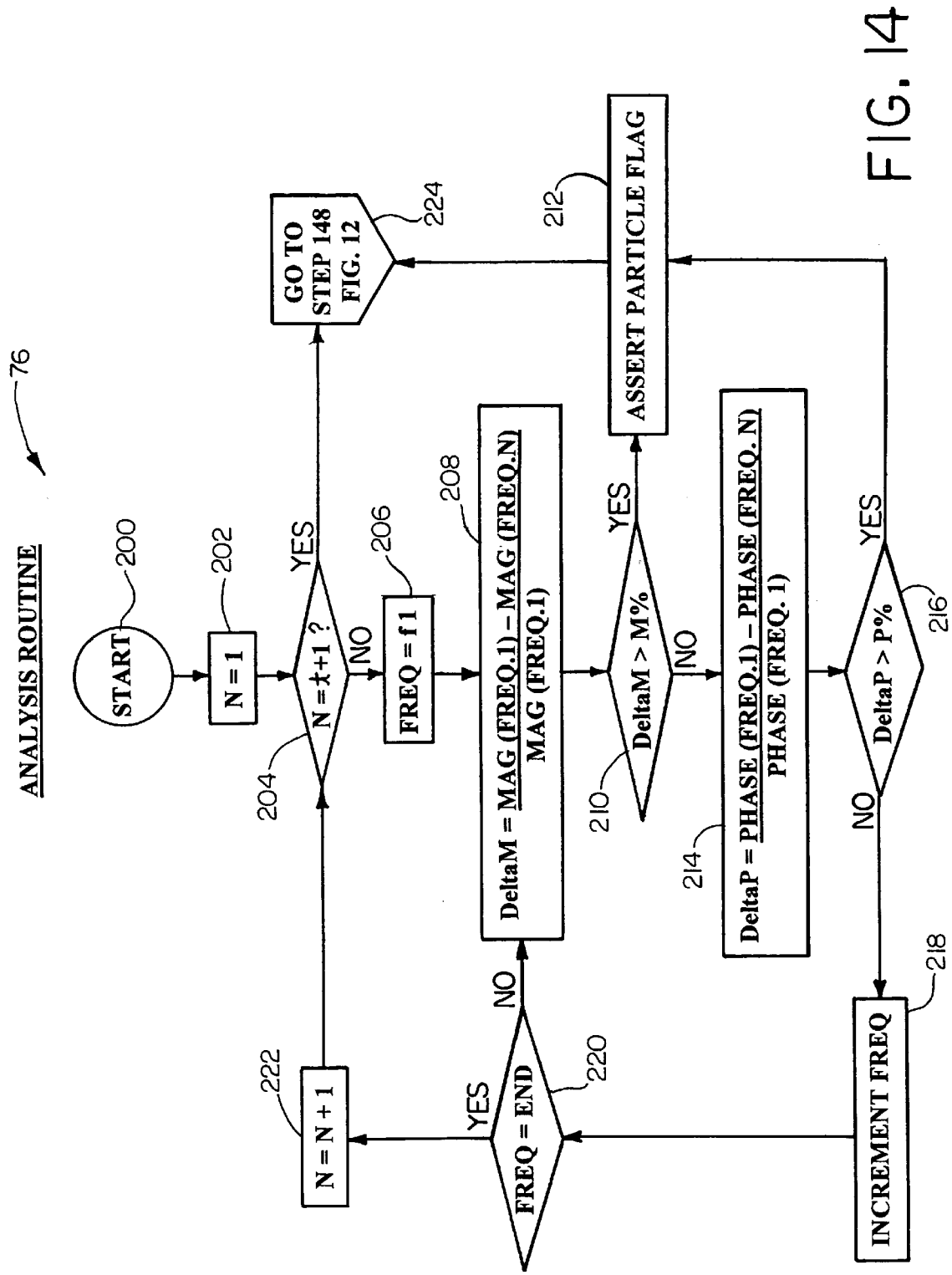
FIG. 14 is a flowchart representing an alternative analysis routine.

Alternatively, another analysis routine as illustrated in FIG. 14, may be utilized to replace steps 126–146 of FIG. 12.

The loop illustrated in FIG. 14 is useful for detecting particles in the sample fluid which tend to settle within the cavity 26 due to gravitational effects. Specifically, the steps shown in FIG. 14 are carried out after obtaining impedance data at each frequency increment (represented by the variable Freq) for multiple (N) frequency sweeps where N=1 to t, and t>1. The routine 76 compares the data collected during the first frequency sweep (N=1) to data collected during other frequency sweeps (N=2, 3, 4, . . . t). If there is a large difference in the measured impedance between any two values at the same frequency, particulates are considered to have been found in the fluid sample and a Particle flag is asserted in the processor 34.

More specifically, the analysis routine 76 begins at start step 200 of FIG. 14. At step 202, the processor 34 sets the counter variable N equal to one corresponding to the first sweep of collected data (N=1). Next, in step 204 the processor 34 checks whether N is equal to "t+1" or one more than the total number of sweeps. If not, the processor 34 proceeds to step 206 in which the processor 34 accesses from the memory 38 the data collected when the frequency was equal to the initial frequency $f_1$ in the first frequency sweep (N=1). The processor 34 then calculates a magnitude difference DeltaM at step 208. The magnitude difference DeltaM is defined as follows:

$$\text{DeltaM} = \frac{\text{MAG (Freq, 1)} - \text{MAG (Freq, N)}}{\text{MAG (Freq, 1)}}$$

where MAG (Freq,1) is equal to the magnitude of the impedance as measured during the first sweep (N=1) at the particular frequency increment represented by the variable "Freq", and MAG (Freq, N) is equal to the magnitude of the impedance as measured during sweep N at the particular frequency represented by "Freq".

Therefore, in step 208 the processor 34 calculates the difference between the measured impedance magnitude at the current frequency increment Freq for the first sweep (N=1) to the measured impedance magnitude at the current frequency increment Freq and sweep number N. Next, in step 210 the processor 34 determines whether the value of DeltaM previously calculated in step 208 exceeds a predefined threshold M% such as, for example, 0.10 or 10%. If yes, the processor 34 proceeds to step 212 in which the processor 34 asserts a Particle flag based on the detection of a large difference between the measured impedance magnitude occurring between the first sweep and a subsequent sweep (indicating the settling of particulate).

If, however, DeltaM is not greater than the predetermined threshold M% in step 210, a second calculation is performed by the processor 34 at step 214. The processor 34 at step 214 calculates a phase difference DeltaP which is defined as follows:

$$\text{DeltaP} = \frac{\text{Phase (Freq, 1)} - \text{Phase (Freq, N)}}{\text{Phase (Freq, 1)}}$$

where Phase (Freq, 1) is equal to the phase of the impedance as measured during the first sweep (N=1) at the particular frequency interval represented by the variable "Freq", and Phase (Freq, N) is equal to the phase of the impedance as measured during sweep N at the particular frequency represented by "Freq".

Therefore, in step 214 the processor 34 calculates the difference between the measured impedance phase at the current frequency increment Freq for the first sweep (N=1) to the measured impedance phase at the current frequency increment Freq and sweep number N. Next, in step 216 the processor 34 determines whether the value of DeltaP previously calculated in step 214 exceeds a predefined threshold P% such as, for example, 0.10 or 10%. If yes, the large change in phase is considered to be indicative of particulate settling and the processor 34 proceeds to step 212 whereby the Particle flag is asserted.

If the phase difference DeltaP at step 216 is not greater than the predetermined threshold, the current frequency Freq is incremented at step 218 to the next frequency in the swept frequency band. At step 220, which follows step 218, the processor 34 determines whether the frequency (Freq) is equal to the end of the frequency band. If not, the processor 34 returns to step 208 and calculates the magnitude difference (DeltaM) for the next frequency in the swept data and again repeats the comparison step at step 210. Again, if the difference in magnitude does not exceed M%, no particle flag is asserted, the processor 34 will again proceed to step 214 and calculate a phase difference (DeltaP) for the next frequency. Again, a comparison will occur at step 216. When the frequency Freq has reached the end of the swept frequency band, as determined at step 220, the processor 34 proceeds to step 222. At step 222, N is incremented to then begin analysis of the impedance data collected during the next frequency sweep as compared with the first sweep. At step 204, once N=t+1, indicating that the last sweep of data has been compared with the first, the processor 34 proceeds to step 224 which return the analysis routine to step 148 of FIG. 12 for trending. The assertion of the particle flag at step 212 may also be displayed at step 170 of FIG. 13 to provide such indication to the user.

After analysis is complete, the processor 34, regardless of which oxidation determination is made (steps 158, 162, 166 and 168) communicates the results to the user via the LCD display 16 or alternatively the I/O port 30 (step 170) and also saves the results by storing them in the memory 38 for subsequent trending analysis, if desired.

Figure 15:
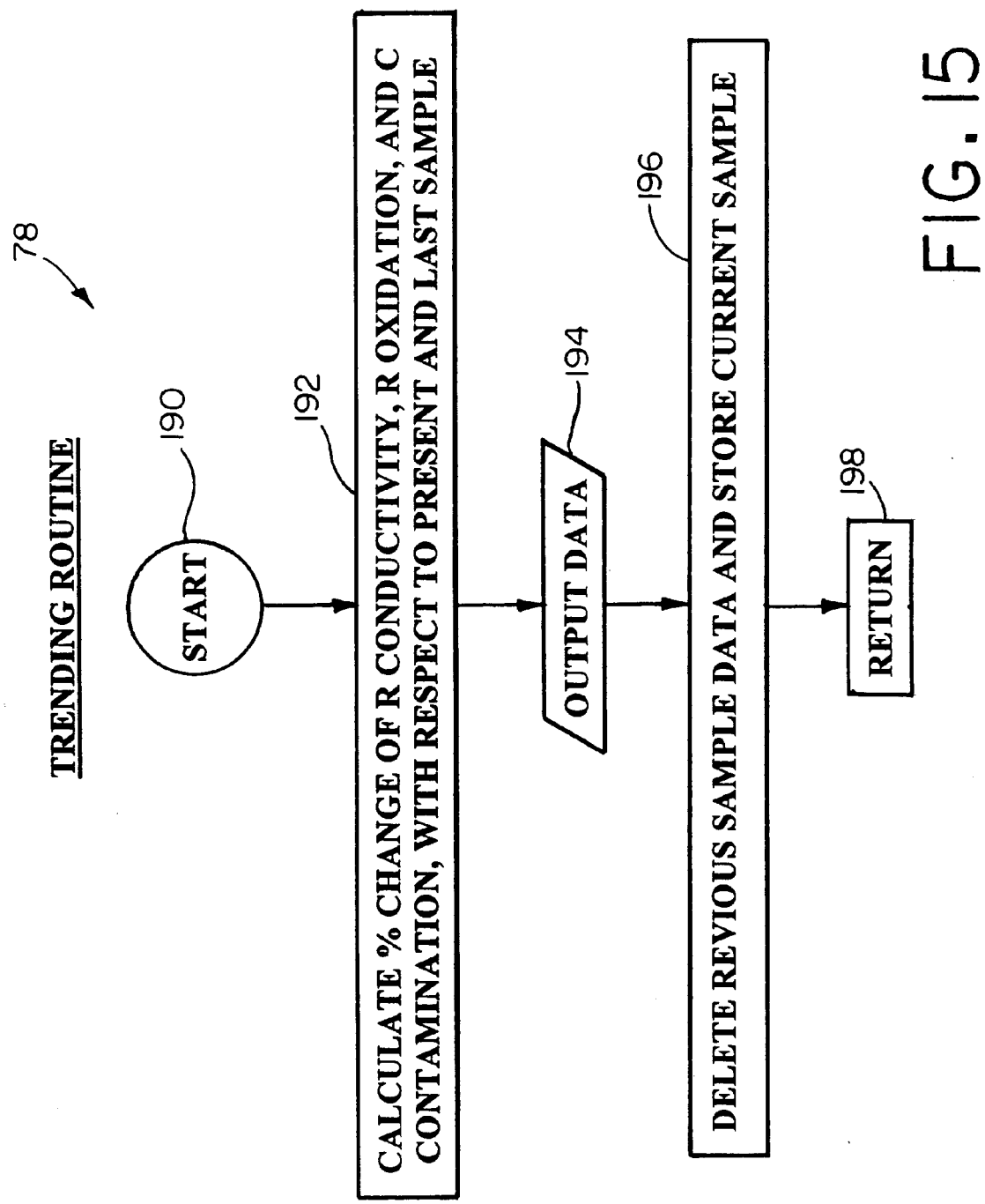
FIG. 15 is a flowchart diagram illustrating an optional trending routine which allows a user to collect and analyze multiple fluid samples for a particular application over time in accordance with the invention.

Upon analyzing the fluid sample data as described above in either the preferred or alternative embodiment, the device 10 provides the user with an option of performing a trending analysis in step 78. FIG. 15 illustrates such trending analysis beginning at step 190. In step 190, the processor 34 queries the user via the display 16 whether any trending calculations are desired. If not, the processor proceeds to step 80 (FIG. 5, not shown in a separate figure) where only the output provided in step 170 (FIG. 13) is displayed. If trending is selected via a user input on the keypad 18, for example, the processor 34 proceeds to step 192 in which it retrieves from memory 38 the value of impedance magnitude and phase over the frequency range and the contamination determination made by the processor 34 as determined for the current sample of the fluid under test and the most recent previous sample of the same fluid (as identified in memory 38 by the SPID and time stamp). Furthermore, in step 192 of the trending routine, the processor 34 calculates the percentage change in the values of the impedance magnitude and phase with respect to the present sample and the last sample of the fluid. This advantageously allows a user to evaluate whether the contamination of a fluid is increasing and at what rate, and develop a history of the contamination of a particular fluid in an application. Such data is output via the display 16 at step 194. At step 196, the processor 34 may be programmed to delete the previous sample data and store only the most recently obtained sample data in the memory 38 in order to preserve memory availability.

In another embodiment, the data from respective fluid samples can be analyzed and trended more thoroughly and efficiently once down-loaded into an external device via the I/O port 30 such as a personal computer which may have more memory and/or computing horsepower. Following step 196, the processor 34 proceeds to step 198 which initiates a return of the processor 34 to step 80 of FIG. 5. In step 80, the processor 34 again displays the results of the sample analysis and trending.

Although the invention has been shown and described with respect to certain preferred embodiments, it is obvious that equivalents and modifications will occur to others skilled in the art upon the reading and understanding of the specification. For example, although the invention has been described primarily in the context of using a capacitive sensor, an inductive or other type sensor could similarly be utilized as will be appreciated.

The present invention includes all such equivalents and modifications, and is limited only by the scope of the following claims.

We claim:

1. A portable fluid screening device, comprising:

a hand-held sized portable housing;

a sensor operatively coupled to the housing for holding the fluid;

circuitry within the housing and operatively coupled to the sensor for measuring a dielectric property of the fluid at each of a plurality of discrete frequency ranges, wherein at least two of the plurality of discrete frequency ranges are in the audio frequency band;

processing means within the housing for determining a condition of the fluid based on the dielectric property of the fluid measured at the plurality of discrete frequency ranges; and a display within the housing which displays information indicative of the determined condition of the fluid.

2. A method of screening a fluid for contaminants, comprising the steps of:

using the fluid as a dielectric;

measuring a dielectric property of the fluid in each of a plurality of discrete frequency ranges, wherein the measuring step further comprises:
measuring the dielectric property of the fluid at a frequency within a first discrete frequency range, wherein the first discrete frequency range is in the audio frequency band;
measuring the dielectric property of the fluid at a frequency within a second discrete frequency range wherein the second discrete frequency range is in the audio frequency band and is different than the first discrete frequency range;

determining a condition of the fluid based on the dielectric property of the fluid measured at the plurality of discrete frequency ranges; and displaying information indicative of the determined condition of the fluid.

3. A fluid screening device, comprising:

a hand-held sized portable housing;

an impedance sensor operatively coupled to the housing and including a cavity for holding a fluid to be screened, an impedance of the impedance sensor being affected by conditions of the fluid;

an impedance measuring circuit within the housing and operatively coupled to the impedance sensor for measuring the impedance of the impedance sensor at a plurality of discrete frequencies, wherein at least two of the plurality of discrete frequencies are in the audio frequency band;

a processor within the housing for processing impedance data taken by the impedance measuring circuit and determining a condition of the fluid; and a display within the housing for displaying information indicative of the determined condition of the fluid.

4. The device of claim 1, wherein the condition of the fluid comprises identification of a specific contaminant, and the display displays information regarding the contamination level.

5. The device of claim 3, wherein the protective body further comprises an input/output port operatively coupled to the impedance measuring circuit for communication with an external processor or memory.

6. The device of claim 5, wherein the input/output port is selected from a group consisting of a serial port, an RF port and an IR port.

7. The device of claim 3, further comprising a variable frequency generator coupled to the impedance measuring circuit, and wherein the impedance measuring circuit is operable to measure the impedance of the impedance sensor over a plurality of frequencies provided by the variable frequency generator.

8. The device of claim 3, wherein the impedance sensor comprises a capacitive sensor.

9. The device of claim 1, wherein the condition of the fluid comprises identification of a specific contaminant, and the display displays information regarding the specific contaminant.

10. The device of claim 3, further comprising a memory associated with the processor for storage of analysis information.

11. The device of claim 3, further comprising input means, wherein the input means is operable to transmit desired user operations to the processor.

12. The device of claim 3, wherein the impedance sensor comprises a pair of interdigitated electrodes formed on a substrate.

13. The device of claim 1, wherein the condition comprises at least one of contamination, water content and oxidation, and the display displays information regarding the at least one of contamination, water content and oxidation.

14. The device of claim 1, wherein the fluid is at least one of a lubricant and a hydraulic fluid, and the processing means is programmed to analyze the at least one of a lubricant and a hydraulic fluid based on the dielectric property of the fluid measured at the plurality of discrete frequency ranges.

15. The device of claim 1, wherein the processing means performs a trending analysis on the condition of the fluid.

16. The device of claim 1, wherein the circuitry comprises a bank of different valued resistors which are selectively coupled to the sensor to form an RC circuit which defines an oscillating frequency of an oscillator included in the circuitry.

17. The device of claim 3, wherein the condition of the fluid comprises a contamination level of the fluid, and the display displays information regarding the contamination level.

18. The device of claim 3, wherein the condition of the fluid comprises identification of a specific contaminant, and the display displays information regarding the specific contaminant.

19. The device of claim 3, wherein the condition comprises at least one of contamination, water content and oxidation, and the display displays information regarding the at least one of contamination, water content and oxidation.

20. The device of claim 3, wherein the processor performs a trending analysis on the condition of the fluid.

21. The device of claim 3, further comprising a connector exposed at a surface of the housing which operatively couples the impedance sensor to the impedance measuring circuit, the connector allowing the impedance sensor to be selectively detached from the housing by an operator without necessitating opening the housing.

22. The device of claim 3, wherein the processor determines the condition of the fluid by comparing the measured impedances at the plurality of discrete frequencies to one another.

23. The method of claim 2, wherein measuring the dielectric property of the fluid at each of the plurality of discrete frequency ranges further comprises measuring the dielectric property of the fluid at a frequency within a third discrete frequency range, wherein the third discrete frequency range is a frequency range above the audio frequency band.

24. The method of claim 23, wherein the frequency in the first discrete frequency range is 1 KHz, the frequency in the second discrete frequency range is 10 KHz, and the frequency in the third discrete frequency range is 200 KHz.

25. The method of claim wherein measuring the dielectric property of the fluid at each of the plurality of discrete frequency ranges comprises:

placing the fluid in a capacitive-type sensor, wherein the fluid forms the dielectric of the capacitive-type sensor and contributes to a capacitance thereof;

coupling the capacitive-type sensor to an oscillator circuit, wherein the capacitance of the capacitive-type sensor influences an oscillation frequency of the oscillation circuit; and identifying the oscillation frequency of the oscillation circuit in each of the plurality of discrete frequency ranges.

26. The method of claim 25, wherein determining the condition of the fluid comprises:

calculating the capacitance of the capacitive-type sensor using the identified oscillation frequency in each of the plurality of discrete frequency ranges;

identifying the condition of the fluid using the calculated capacitance in each of the discrete frequency ranges.

27. The method of claim 26, wherein identifying the condition of the fluid using the calculated capacitance in each of the discrete frequency ranges comprises:

plotting a capacitance curve over frequency using the calculated capacitance in each of the discrete frequency ranges;

comparing the capacitance curve to one or more reference capacitance curves, wherein the reference capacitance curves represent one or more fluids having known contamination conditions associated therewith; and determining the condition of the fluid using the comparison.

28. The method of claim 27, wherein comparing the capacitance curve to one or more reference capacitance curves comprises:

identifying a rate of change of capacitance over frequency for the capacitance curve and a reference capacitance curve; and comparing the rates of change of capacitance of the capacitance curve and the reference capacitance curve over frequency.

29. The method of claim 27, wherein comparing the capacitance curve to one or more reference capacitance curves comprises:

performing a statistical correlation between the capacitance curve and each of the one or more reference capacitance curves; and identifying one of the one or more reference capacitance curves which has a largest correlation with the capacitance curve.

30. The method of claim 29, further comprising the steps of:

coupling a known reference capacitance to the oscillation circuit;

identifying the oscillation frequency of the oscillation circuit in each of the plurality of discrete frequency ranges;

calculating a capacitance associated with the known reference capacitance using the identified oscillation frequency in each of the plurality of discrete frequency ranges;

determining a compensation value by comparing the calculated capacitance to the known reference capacitance; and using the compensation value in determining the condition of the fluid.

* * * * *